(12) United States Patent
LaBorde

(10) Patent No.: US 10,811,123 B2
(45) Date of Patent: Oct. 20, 2020

(54) PROTECTED HEALTH INFORMATION VOICE DATA AND / OR TRANSCRIPT OF VOICE DATA CAPTURE, PROCESSING AND SUBMISSION

(71) Applicant: David LaBorde, Norcross, GA (US)

(72) Inventor: David LaBorde, Norcross, GA (US)

( * ) Notice: Subject to any disclaimer, the term of this patent is extended or adjusted under 35 U.S.C. 154(b) by 1949 days.

(21) Appl. No.: 14/228,739

(22) Filed: Mar. 28, 2014

(65) Prior Publication Data

US 2015/0278449 A1 Oct. 1, 2015
US 2018/0004898 A9 Jan. 4, 2018

Related U.S. Application Data

(60) Provisional application No. 61/806,192, filed on Mar. 28, 2013.

(51) Int. Cl.
| | |
|---|---|
| *G16H 10/60* | (2018.01) |
| *G06Q 50/24* | (2012.01) |
| *G06Q 20/14* | (2012.01) |
| *G06F 21/62* | (2013.01) |
| *G06F 19/00* | (2018.01) |
| *H04W 12/06* | (2009.01) |
| *H04L 29/06* | (2006.01) |
| *H04W 12/02* | (2009.01) |
| *H04W 88/02* | (2009.01) |

(52) U.S. Cl.
CPC ............. *G16H 10/60* (2018.01); *G06F 19/00* (2013.01); *G06F 19/328* (2013.01); *G06F 21/6245* (2013.01); *G06Q 20/14* (2013.01); *G06Q 50/24* (2013.01); *H04L 63/0861* (2013.01); *H04W 12/02* (2013.01); *H04W 12/06* (2013.01); *H04W 88/02* (2013.01)

(58) Field of Classification Search
CPC .. G06F 19/322; G06F 19/328; G06F 21/6245; G16H 10/60; G06Q 50/24; G06Q 20/14
See application file for complete search history.

(56) References Cited

U.S. PATENT DOCUMENTS

| | | | |
|---|---|---|---|
| 5,579,393 | A | 11/1996 | Conner |
| 7,353,238 | B1 | 4/2008 | Gliklich |
| 2001/0032215 | A1 | 10/2001 | Kyle |
| 2002/0019749 | A1* | 2/2002 | Becker ............... G06F 19/325 705/2 |
| 2002/0123907 | A1 | 9/2002 | Strayer |
| 2005/0251417 | A1 | 11/2005 | Malhortra |
| 2005/0288965 | A1 | 12/2005 | Van Eaton |
| 2006/0053034 | A1 | 3/2006 | Hlathein |
| 2006/0229911 | A1 | 10/2006 | Gropper |
| 2007/0143148 | A1 | 6/2007 | Kol |
| 2007/0188774 | A1 | 8/2007 | Yudasaka |
| 2008/0133269 | A1 | 6/2008 | Ching |
| 2009/0132586 | A1 | 5/2009 | Napora |
| 2009/0164236 | A1 | 6/2009 | Gounares |

(Continued)

*Primary Examiner* — Vivek D Koppikar
*Assistant Examiner* — Minnah Seoh
(74) *Attorney, Agent, or Firm* — Culpepper IP, LLLC; Kerry S. Culpepper

(57) ABSTRACT

A system and method that permits a user to utilize a means of capturing and managing one or more voice files containing speech utterances ("Voice Utterances") and/or the corresponding transcript ("Transcript") containing protected health information (PHI) on a mobile device.

5 Claims, 29 Drawing Sheets

(56) References Cited

U.S. PATENT DOCUMENTS

| | | |
|---|---|---|
| 2010/0122179 A1 | 5/2010 | Nakamura |
| 2010/0161345 A1 | 6/2010 | Cain |
| 2010/0305966 A1 | 12/2010 | Coulter |
| 2011/0110568 A1 | 5/2011 | Vesper |
| 2011/0153351 A1 | 6/2011 | Vesper |
| 2012/0173281 A1 | 7/2012 | DiLella |
| 2013/0054260 A1 | 2/2013 | Evans |
| 2013/0096938 A1 | 4/2013 | Stueckemann |
| 2013/0307955 A1 | 11/2013 | Deitz |
| 2014/0249860 A1 | 9/2014 | Rynchek |

* cited by examiner

| Cancel | New Bill |

Doe, Mary
MRN 5678900
DOB 04/25/1935                          Edit

Myocardial infarction (410.9)

Select E/M type (CPT)

Select procedure codes (CPT)

TAKE PHOTO OF FACESHEET/CHARTING/OTHER

○ Face sheet

COMPLETE BILL VIA VOICE / ADD A VOICE MEMO

○ Transcript 1 [Full Bill] 06/21/2012

CANCEL        NEXT

Memo icon (note pad) shows. If they click on row, takes them back to editor / recording screen.

Carrier 🌐      8:36 PM      🔋

Touch screen to focus.

PATIENT INFORMATION SHEET
Patient Sheet Number: 0000000781    Date: 14-16-1994
Name : Carrier, Julie    Social Security #: 333-33-3333
Address: 123 Panton Street    Fax #:    Telephone: 0404014
City: Atlanta    State: OA    Zip: 12345

Name:    Phone:

Phone number: 500 555 1212

Phone Number

Are you diabetic? YES___NO___
Diagnostic___

If you___ YES___

Patient Insurance Information

Insurance Company: Medicare
ID Number: 333-333-3333
Group:

Facesheet

Cancel      Take Picture

PROTECTED HEALTH INFORMATION VOICE DATA AND / OR TRANSCRIPT OF VOICE DATA CAPTURE, PROCESSING AND SUBMISSION

STATEMENT OF RELATED APPLICATIONS

This application claims the benefit of U.S. Provisional Patent Application No. 61806192 having a filing date of 28 Mar. 2013.

BACKGROUND

Technical Field

The present application generally relates to heath information voice data and/or transcript of voice data and more specifically to the capturing, processing, and submission of this data from a mobile device.

Prior Art

Protected Health Information is defined by the US Health Insurance Portability and Accountability Act (HIPAA). Interpretations of what PHI might include can be found on Wikipedia en.wikipedia.org/wiki/Protected health information as accessed 03.28.2013; HIPAA.com, as accessed on 03.28.2013; and from many other $3^{rd}$ party information sources.

The US government generally requires that systems accessing electronic health records need to be configured to grant access to PHI only to people who need to know it. If PHI is accessed by a person not authorized to access it, then this could indicate a violation of both the HIPAA Privacy and Security Rules. Under certain circumstances, such an incident may have to be reported to the US Department of Health and Human Services (HHS) and/or a state agency as a breach of unsecured protected health information. Having good access controls and knowledge of who has viewed or used information (i.e., access logs) can help to prevent or detect these data breaches.

BRIEF SUMMARY

Briefly, the invention addresses challenges presented by a mobile provider workforce that sees patients within and across complex healthcare organizations which are frequently remote from the location where the healthcare insurance reimbursement claims are prepared and submitted. The invention accomplishes this by enabling on-the-go healthcare providers to capture and submit information about services rendered from any location via multiple modalities available on a mobile device. By using the technology, health care providers and healthcare provider organizations can accelerate clinical and administrative workflows, leading to more streamlined and timely medical claim generation and submission.

For example a small private practice doctor can transmit billing information from the hospital to his or her back office by taking a photograph of the patient identifiers/insurance information and annotating that with speech derived data and manual data entry (i.e., annotate with billing codes or description of services provided) without the need for the implementation of a costly integration between a hospital information system and his back office (practice management) information system. The invention allows this to be done on a mobile device and in a way that is secure and in compliance with HIPAA privacy and security regulations. As such, the hospital can feel comfortable in that the provider is using a secure means to do this. In fact, users of the system may be the hospital's own employees and they may simply be transmitting data from one area or business unit or operation of the hospital to another (i.e., from the clinical side at the point of care to the billing operations in the back office). The hospital may prefer this system be used as opposed to simply having users doing this via renegade unapproved and non-secure means, such as taking photographs on their phone that end up stored unencrypted and non-password protected or texting protected patient information in clear text via SMS texting.

The invention can comprise the following basic steps:

1. Take a photograph of the key demographics of the patient (name, date of birth, account number, medical record number, gender, etc. or generally patient identification information), often from a patient sticker or a hospital facesheet;

2. Allow a user to make additional annotations to this information (description of services rendered and/or the actual diagnosis and billing codes, location of the services, etc.);

3. Securely parse or extract this patient identification information (potentially initially locally on the device but in the long run remotely in a data center and NOT on the device, i.e., wipe it from the device) and transmit it to a charge capture manager device at a back end system where it is stored securely at rest in a charge database;

4. Process this information via a combination of machines with or without human quality assurance, with the process being turning the data in the image to structured data persisted in data transport objects (data set) and some sort of data repository (charge database); and 5. Transmit, provide access to, or present the information for consumption in a downstream business process, i.e., creating a medical claim. This can range from allowing an employee or medical billing staff member to pull up the information (i.e., look at it on a screen) from the charge database via the charge capture manager device to sending the information via an application programming interface or via a standard communications protocol like HL7 or Electronic Data Interchange (EDI) transaction (i.e., an EDI 5010 transaction) to a downstream system (i.e., a practice management software or a claims clearing house on another client device).

Accordingly, there is a need for a system and method for capturing, processing, and submission of this information, data, and images from a mobile device in a simple and secure manner, thereby simplifying the information collection and billing process for professionals, such as physicians. It is to this need and other needs that the present invention is directed.

BRIEF DESCRIPTION OF THE DRAWINGS

FIG. 3 illustrates an example workflow of user adding a memo addendum to a 'bill', or an accounting of services rendered to a patient during a care episode, by voice—step one: initiate " . . . add a voice memo . . . " process.

FIGS. 6-26 illustrate an example application or "app" on a smart phone, showing a series of screen captures of the invention in use.

DETAILED DESCRIPTION OF PREFERRED EMBODIMENTS

Figure 1:
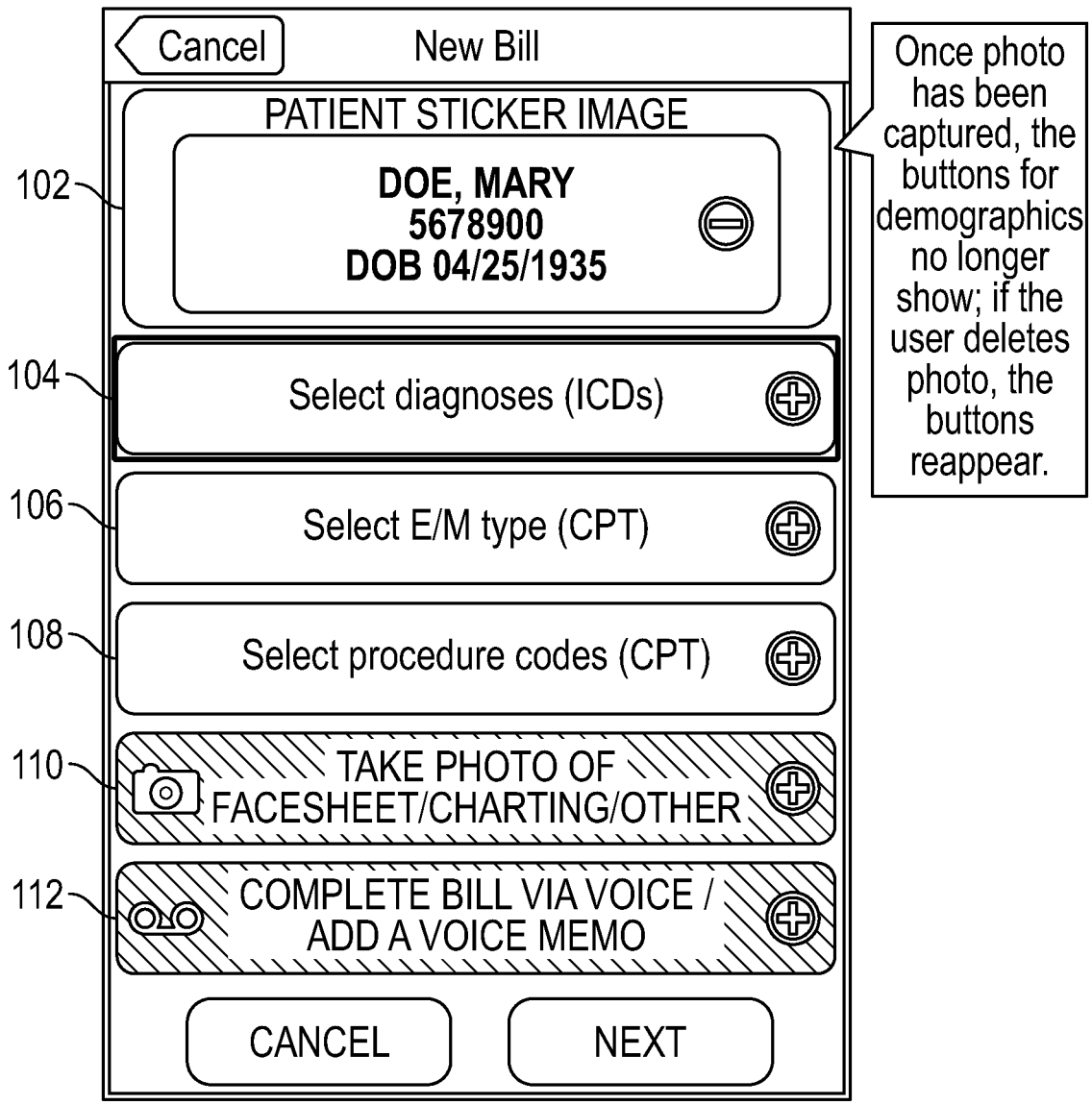
FIG. 1 illustrates an example workflow of user adding diagnosis information (diagnosis codes) by voice—step one: initiate "Select diagnoses . . . " process.

Generally, the present disclosure concerns a HIPAA compliant component of a mobile technology solution that enables healthcare providers and health care provider organizations to improve provider workflow, capture more revenue and obtain payment faster in the revenue cycle and eliminating inefficiencies, interim steps, and delays in information gathering (from multiple sources and physical locations) and submission.

The focus of the technology is to address challenges presented by a mobile provider workforce that sees patients within and across complex healthcare organizations (many which have multiple locations and are on different information systems) which are frequently remote from the location where the healthcare insurance reimbursement claims are prepared and submitted.

The technology accomplishes this by enabling on-the-go healthcare providers to capture and submit information about services rendered from any location via multiple modalities available on a mobile client device, including, but not limited to, computer vision and speech. For example, a physician lounge, a physician's residence, a physician's desk in their office, or a point of care where a patient can be seen including, but not limited to, the patient's home, a nursing home, an ambulatory or outpatient surgery center, a non-hospital based clinic or office where a patient is seen on an outpatient basis, a hospital unit or area, including, but not limited to, an intensive care unit, medical or surgical floor, step down unit, emergency room, pre-operative area, post operative area or post anesthesia care unit, procedure area, ambulatory clinic, operating room, etc. By using the technology, health care providers and healthcare provider organizations can accelerate clinical and administrative workflows, leading to more streamlined and timely medical claim generation and submission.

The mobile technology solution is a component of a broader platform that includes backend endpoints that communicate with mobile client devices equipped with multiple peripherals including, but not limited to, a graphical user interface and touch screen, a means of image capture, a means of voice capture, a transceiver, controller and instructions for configuring the controller stored in a memory.

The platform enables on-the-go healthcare providers to immediately or in a queued or batched process submit via a client device data including, but not limited to, patient demographic, diagnosis, and billing information to a charge capture manager device at a backend endpoint that enables (i) staff members in a back office location (where financial and administrative operations are carried out for the healthcare provider organization) to access, edit, and further annotate the data set via a client device; (ii) a $3^{rd}$ party system (for example, a practice management software, a claims clearing house, or a payor organization) to securely access or be sent all or a subset of the data via a client device; and (iii) the data to be sent on for further downstream processing by a machine and or human. The data can include, but is not limited to, medical diagnosis and billing codes, health insurance information, charting related to what service(s) were rendered, etc.

An example of how the technology might be used allows physicians and other healthcare providers to 'Touch, Talk, and Submit' billing data eliminating the need for paper-based billing cards and manual data entry. In this example, the client device 10 is a mobile device. The application (mobile device app) is installed in the memory 1006 of the mobile device. The controller 1004 is configured according to the mobile device app stored in the memory 1006. Patient demographics, diagnosis information, and detail about the services rendered needed for billing can be captured via image and voice. Billing codes can be picked from a list returned from a voice query. The data is encrypted, and instantaneously or in a batch fashion, delivered to the provider organization's billing staff or a $3^{rd}$ party company that does billing on behalf of the provider and ultimately to the payor via a connection to a network 15. As shown in, for example, FIG. 5, the mobile device app may present a template for providers to follow regarding what information is needed and provide the ability to securely capture patient demographics and healthcare insurance billing information with the smart phone camera (leveraging computer vision) from a wristband, a computer screen showing the patient's demographics or insurance information, a sticker or paper with the patient's demographics and/or healthcare insurance information, and/or digital or paper face sheet. The solution eliminates the need for paper based charge capture processes, which result in lost revenue, errors, and significant delays in claim generation and submission.

A description of the technology—protected health information voice data and/or transcript of voice data capture, processing and submission is:

A system that permits a user (that may be required to undergo authentication and authorization to access this resource) to utilize a means of capturing and managing one or more voice files containing speech utterances ("Voice Utterances") and/or the corresponding transcript ("Transcript") containing protected health information (PHI) on a mobile client device Permit none or some user and/or hardware/software driven post PHI Voice Utterance and/or related Transcript(s) capture processing on mobile client device Send encrypted PHI Voice Utterance(s) and/or the meaningful content of related Transcript(s) derived after post PHI Voice Utterance capture processing and/or Transcript generation via a secure wired or unwired communication medium and/or protocol (if and when a connection is confirmed to be available) in real-time or via a queued or batched process either standalone or as annotation to a broader dataset Securely receive PHI Voice Utterance(s) and/or related Transcript(s) at a wired or remote backend endpoint (charge capture manager device)

Maintain an encrypted copy of PHI Voice Utterance(s) and/or related Transcript(s) for some period of time on local (mobile) client device or securely remove and/or destruct and/or overwrite all data related to the PHI Voice Utterance(s) and/or related Transcript(s) from the local (mobile) client device after confirming successful transmission of the PHI Voice Utterance(s) and/or related Transcript(s) to the charge capture manager device at the remote backend endpoint Permit none or some authenticated and authorized user and/or hardware/software driven post PHI Voice Utterance(s) and/or related Transcript(s) receipt processing of PHI Voice Utterance(s) and/or related Transcript(s) on a machine and/or by an authenticated and authorized user via a secure user interface affiliated with the wired or remote backend endpoint Securely store PHI Voice Utterance(s) and/or related Transcript(s) and/or some or all of the meaningful content of thereof derived after post processing Securely log (for future audit purposes) any and all access to or transmission of PHI Voice Utterance(s) and/or related Transcript(s) and/or some or all of the meaningful content of thereof derived after post processing Process may stop here or a means may be provided to:
  Securely play back the PHI Voice Utterance(s) and/or render the related Transcript(s) and/or some or all of the meaningful content of thereof derived after post processing in a user interface on some user client machine or device (client device)
  Securely pass PHI Voice Utterance(s) and/or related Transcript(s) and/or some or all of the meaningful content of thereof derived after post processing to a downstream internal process
  Securely route or make available the PHI Voice Utterance(s) and/or related Transcript(s) and/or some or all of the meaningful content of thereof derived after post processing to an authenticated and authorized $3^{rd}$ party system via some application programming interface
  Securely remove and/or destruct and/or overwrite all data related to the PHI Voice Utterance(s) and/or related Transcript(s) from the charge capture manager device at the backend endpoint after receiving instructions either programmatically or from an authenticated and authorized user with a role that has data deletion privileges Following is a disclosure of an illustrative application of the invention, presented in the form of a demonstration and referring to the figures.

In one embodiment, the mobile solution includes an application for a smart phone or the like (referred to here generally as client device). The physician simply verbally provides information about the care rendered to a patient and then they hit submit. The application is installed on the client device 10 that is HIPAA compliant. The solution leverages voice and computer vision to get information into the system, which means that there is no need to integrate the solution in the hospital, although a hybrid strategy of back end hospital system integration and image based data recognition is envisioned.

Currently, the status quo process of how physicians capture charges today for the work they do, namely, the patient care they provide, in a hospital, in an office, in an ambulatory surgery center, or in a nursing home. After a patient is seen, for example an obese hypertensive patient with hypertension who came into the office for treatment of an ankle sprain, the doctor charts in the medical records system, be it paper or electronic. That is either in the facility's record system or if in the doctor's office, in the doctor's own records system. Associated with that visit, the doctor needs to translate that care into billing codes. Billing codes consist of diagnosis codes as well as codes for the evaluation and management and any procedures that may have been done. Here at the top of the currently used form, often termed a superbill, there is a space where basic demographics can be captured. Name, date of birth, date of service, account number, and sometimes medical record number. Immediately beneath that, the doctor can write down the diagnosis codes, such as International Classification of Diseases (ICD)-9 codes and soon to be ICD-10. The rest of the form is dedicated to capturing evaluation and management charges about the visit. Those are called Current Procedural Terminology (CPT) codes. If this were an office visit, the doctor can look under outpatient services and they simply check off what they did and what the related diagnosis was.

These forms are typically created with the most common billing diagnosis and billing codes that doctor might use. By having the most common codes on the forms, the doctor can simply check off the form to indicate to the billing staff in the back office, which of the codes is correct. Above the diagnoses on a typical superbill form are the CPT codes, whether for a new patient, an established patient, a consult, a post-operative visit. These are the codes with a straightforward low, moderate, or high complexity, etc., diagnosis or treatment. The doctor checks off the appropriate codes, and the related diagnoses. The typical form has a box for patient label. In the hospital there are frequently stickers that the doctors can pick up to quickly provide and capture the demographics for the care by attaching the sticker on the form. The use of such stickers allows the various forms to contain much of the same evaluation and management codes for the inpatient setting so the doctor can check them off. Using the stickers also can allow for the capture of where the patient was seen and what physician rounded on that patient. There are multiple examples of stickers, such as bracelets or wristbands that are worn by the patient to confirm before pills are provided, before a procedure is done, that the patient is indeed the correct patient to be receiving that procedure, diagnosis, or medication. Doctors always capture these stickers to know who they saw in the hospital.

There are many varieties of the paper work or paper types that doctors use to capture charges in the hospital. For example, on such a form, a doctor would attach a sticker on and then the doctor would place a check next to the appropriate CPT code. Here the doctor can indicate what facility they are seeing the patient at, and write in their name as far as which physician saw the patient. That is the current process. It is a paper driven process and the doctor is responsible for carrying the form or superbill and placing it in a bin or delivering it personally to the back office so that charges can then be generated in the form of claims that go off to the payor. Some doctors simply carry around a piece of paper during the course of their day and attach stickers on the paper. In that way the doctors have a record of who they saw, and they did not have to write anything down.

The other important piece of paper work is one that originates in the hospitals and skilled nursing facilities if the doctor is doing nursing home rounds. This is often referred to as a face sheet. The primary important information beyond the basic demographics that the face sheet has includes information on the admission, information about who the guarantor is on the insurance, and the insurance information that shows who the payor is and what the related group number and policy numbers are, all of which is information that is required so that physicians can do their billing.

The physician revenue cycle all starts with a patient being seen. After that patient is seen, on the administrative side in so far as the billing, one of these paper forms must then make it to the biller. This is the front end of the revenue cycle. This is where this paper, such as the superbill, billing card, or encounter form, is filled out. This is also where delays can accrue if the physician takes a long time to turn in the paper work. Once those charges are in the back office, a biller can then process them and enter the claims into the practice management software. At that point, the charges on the claim go off to the payor through a claims clearing house and if everything goes well, there will be a payment that comes out of the back end of the revenue cycle process.

The present invention focuses on eliminating the front end of the charge cycle, taking the charge lag of the physician revenue cycle from 10-30 days down to zero days. The physician opens the mobile client device or desktop app (application) and logs in. Particularly, the controller 1004 of the client device 10 executing the application generates a resource request including an authentication credential associated with the physician (user) to be sent to the charge capture manager device 20 via a connection to the network 15. Upon logging in, one option the physician has is to view their bill history where they can see which patients (one or more patient identifications) they have created bills on, what the medical record number and facility were for those patients, when the charge was submitted and the current status of the charge, whether the biller has posted the charge to the practice management software and sent the charge off to the claims clearing house and then the payor, or whether the charge is still a new charge. This allows the doctor to have some direct visibility into the revenue cycle.

Figure 5:
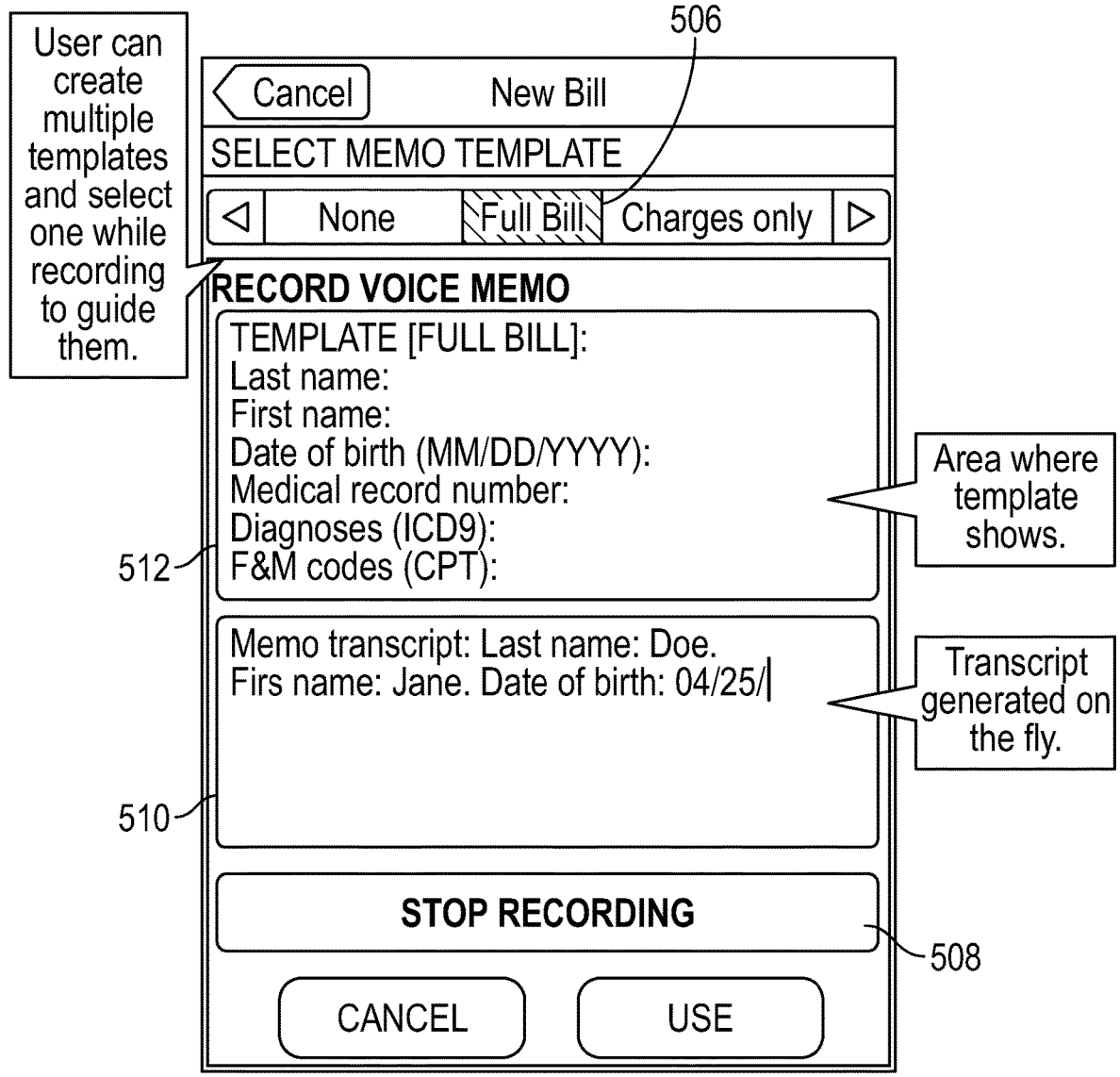
FIG. 5 illustrates an example workflow of user adding a memo addendum to a 'bill', or an accounting of services rendered to a patient during a care episode, by voice—speak memo, transcript of utterances is returned as body of memo, use template as a guide if desired, save memo and submit to back office with the patient charges or 'bill.'
Figure 7:
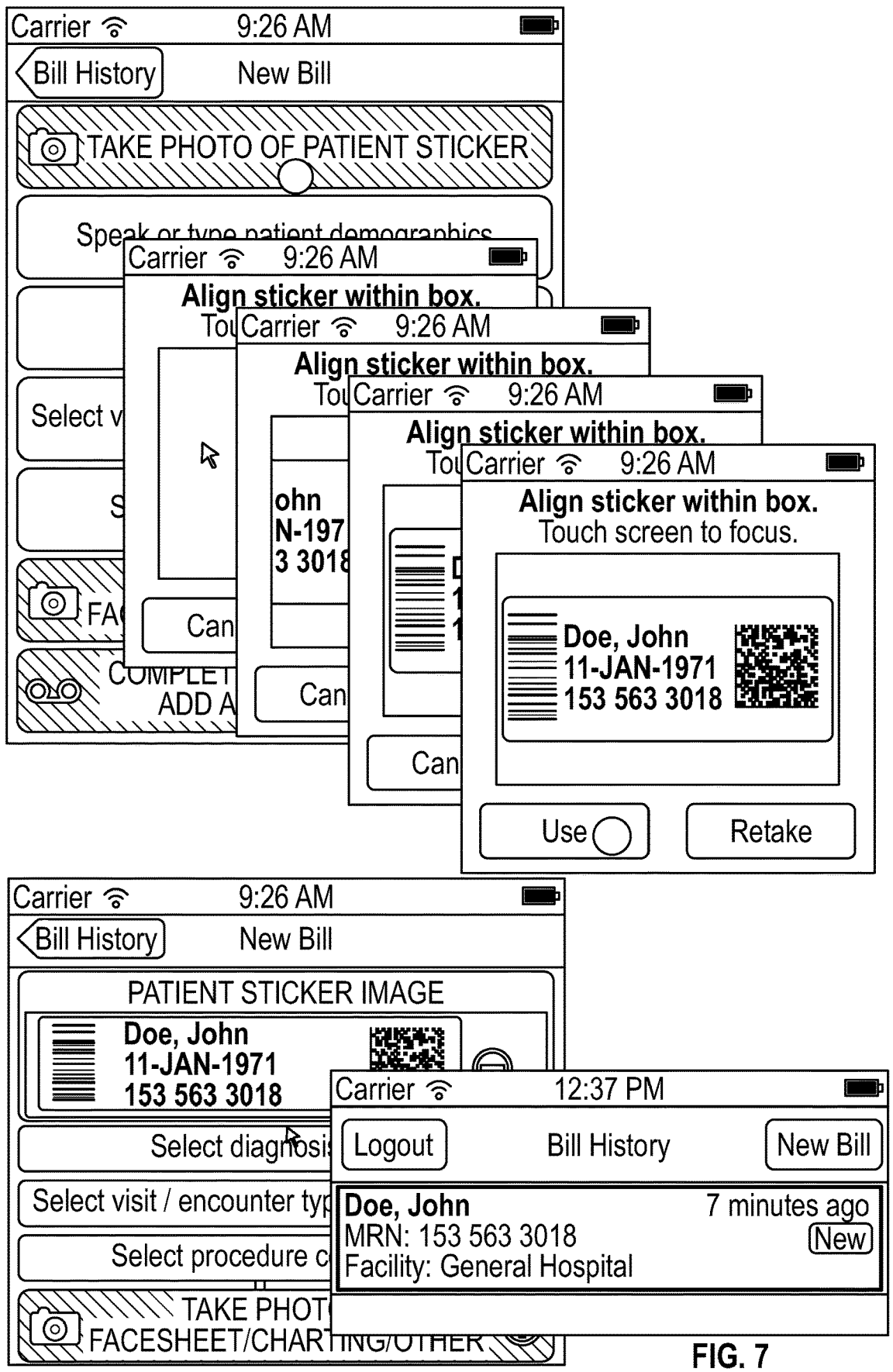

Most of the time, the provider is logging into the application on the client device 10 to do one thing, that is, create a new bill or charge. This is accomplished via the primary bill creation interface/workflow (new bill graphical display) for the doctor. Referring to FIG. 1, this process can start with the ability to leverage the patient sticker or patient identification bracelet or wristband in the hospital to capture the demographics using computer vision. The new bill graphical display includes an image graphical interface 110, wherein an image input interface 102 is generated when the image graphical interface 110 is selected for receiving an image including patient identification information. The doctor simply takes a photo of patient sticker after the doctor is prompted to take a picture of the patient sticker by the app. For example, the doctor centers the lens over the sticker and once satisfied, they take the picture as shown in FIGS. 15-18. The doctor then has the opportunity to review the photograph, to perform quality assurance, to ensure that it is not blurry, etc. The doctor is prompted: 'can you read this?' If the doctor is satisfied and approves of the image quality, the doctor clicks the use (approve image) button and a thumbnail image of that patient sticker is then added to the bill. The thumbnail of the patient sticker image would then appear in the area of the create new bill workflow interface as shown in FIG. 7. If the doctor does not happen to be around or near a sticker, the doctor can always speak or type in the patient demographics. If the medical provider prefers voice to text technology, this can be used to create or capture the patient's basic demographics without touching the typewriter or keyboard on the device at all. The new bill graphical display includes a voice input graphical interface 112, wherein a voice input display shown in FIG. 3 subsequent in hierarchy to the new bill graphical display is generated when the voice input graphical interface 112 is selected. The voice input display includes a record control graphical interface 408 for recording voice utterances including patient identification information when selected; a transcript display portion for displaying a transcript of the voice utterances; and a plurality of template graphical interfaces for categorizing information included in the voice utterances to extract the patient identification information. Referring to FIG. 5, in this example a doctor selects the full bill template graphical interface 506 so that the associated full bill template 512 is displayed. The doctor is speaking a fictional patient's name and basic demographics would be "Jane . . . next field (navigating the data capture form in the user interface) . . . Doe . . . next field . . . female (adding the patient's gender) . . . next field . . . Nov. 1, 1942 (adding the patient's date of birth) . . . next field . . . 305862 (adding the patient's medical record number) . . . 688922 (adding the patient's account number)" The software application on the mobile device or desktop then transcribes the provider's verbal utterances which is generated and shown on the fly in the transcript display portion 510. Once that process has been completed, those basic patient demographics have been populated in the app.

Figure 2:
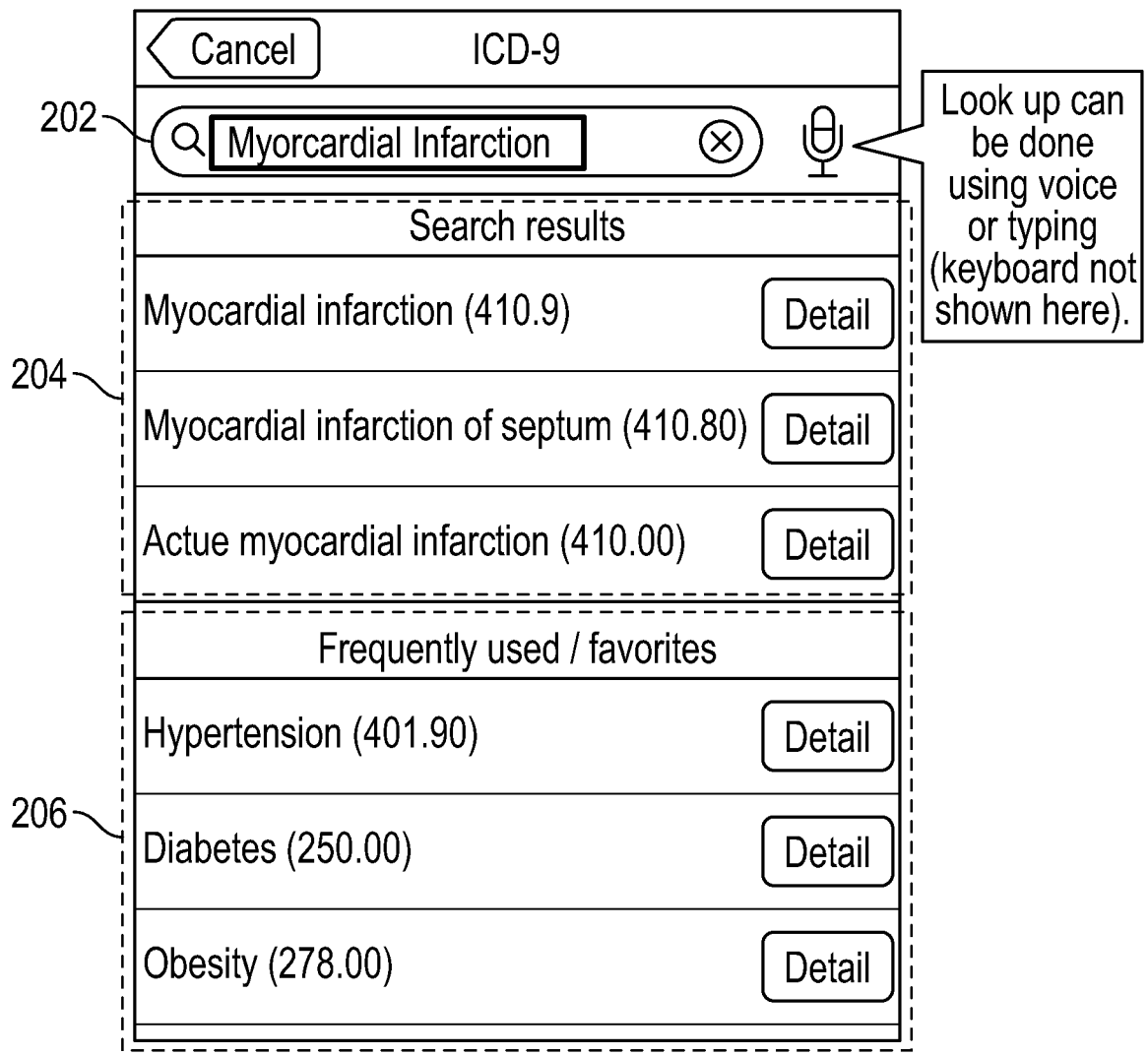
FIG. 2 illustrates an example workflow of user adding diagnosis information (diagnosis codes) by voice—step two: speak diagnosis, transcript of utterance is returned, a query is initiated and a list of results from which user can choose a match is returned.
Figure 4:
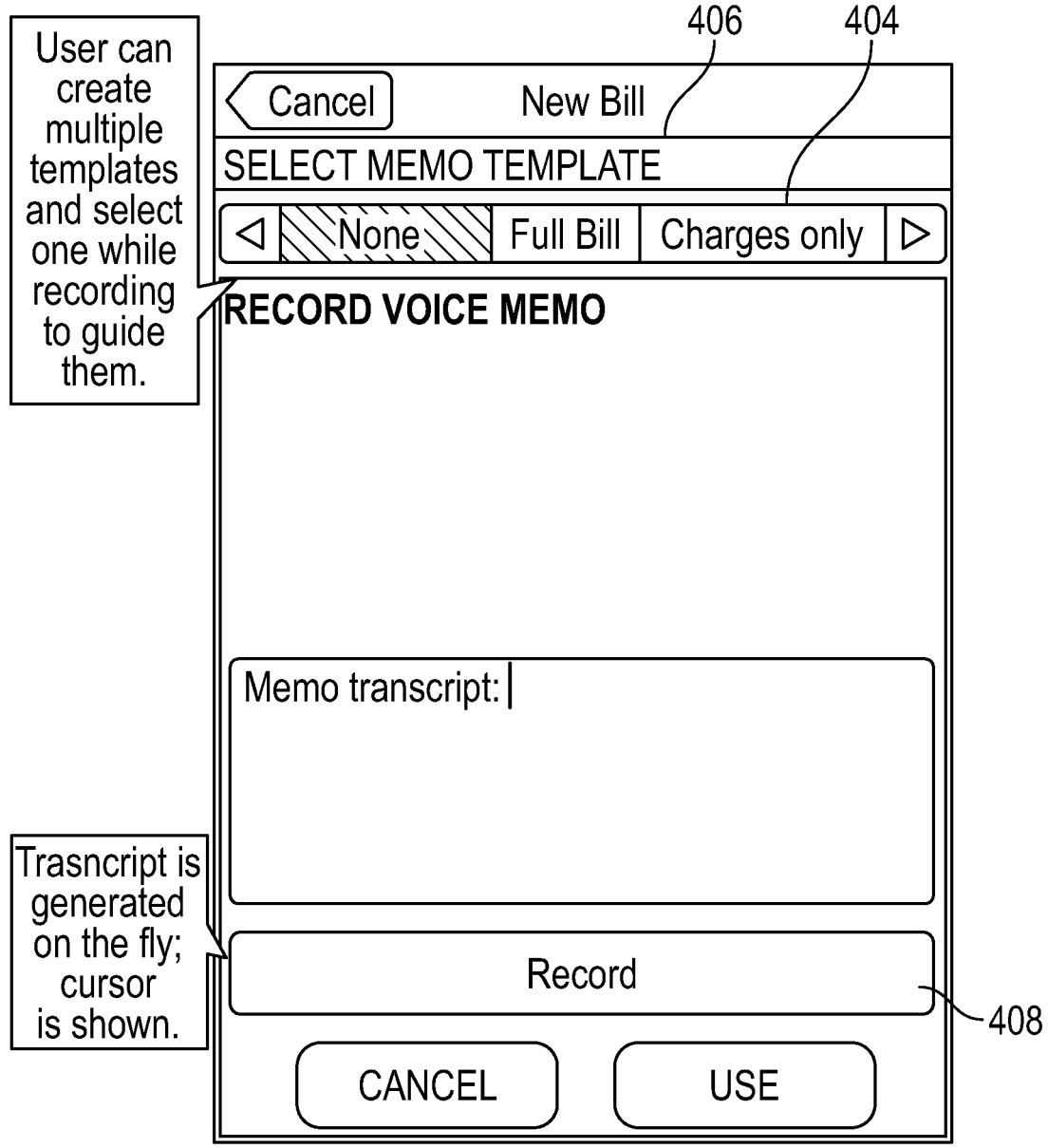
FIG. 4 illustrates an example workflow of user adding a memo addendum to a 'bill', or an accounting of services rendered to a patient during a care episode, by voice—step two (optional): select a 'prompting' template.

The provider then has the opportunity to select the related diagnoses for the visit, either by speaking into the client device or by selecting matching billing codes from a list of results that the software application returns in response to the doctor's verbal utterances. The new bill graphical display includes a diagnosis selection graphical interface 104, wherein a diagnosis selection display shown in FIG. 2 is generated when the diagnosis selection graphical interface 104 is selected, the diagnosis selection display subsequent in hierarchy to the new bill graphical display, the diagnosis selection display including: an open text field 202 for receiving diagnosis related information; a results display 204 for displaying a plurality of diagnosis codes returned as search results based upon the diagnosis related information; and a favorites display 206 for returning a plurality of diagnosis codes selected more than a predetermined number of times in a predetermined previous time period or diagnosis codes previously designated as favorite diagnosis codes. For example, if the doctor speaks or selects "hypertension", a list of billing code search results is returned in response and then the doctor selects matching billing code. Here again the doctor can leverage voice to text to verbally look up the desired billing codes by speaking. The doctor can enter or add as many of the diagnosis billing codes as they need to by speaking or selecting, for example, "diabetes", and a list of billing code search results is returned in response. The doctor can continue with additional diagnoses to accurately capture what is going on with the patient ("obesity", "sprained right ankle", etc.).

Returning to FIG. 1, then the doctor can select the evaluation and management (E/M) code selection graphical interface 106 to create or add an evaluation and management billing code, such as "new inpatient consultation". When the E/M code selection graphical interface 106 is selected, an E/M code selection display subsequent in hierarchy to the new bill graphical display is generated, the E/M code selection display including a plurality of selectable CPT codes. The invention allows that anything in the billing code database (on the client device 10 or on the charge capture manager device 20) that matches what the physician has said or selected will be returned in the list of results in the pick list shown in the user interface in response to the physician's input. The doctor can then select the correct billing code. Similarly, when the plurality of diagnosis codes returned as search results as described above, the diagnosis codes can include International Classification of Diseases 9 (ICD-9) diagnosis billing codes and but also the corresponding ICD-10 diagnosis billing code. The present inventive solution is ICD-10 ready, which is a major issue, the transition from ICD-9 to ICD-10, facing hospitals and physicians. ICD-10 is slated to go live in Oct. of 2014.

Finally, if a procedure was done on the patient during the encounter with the provider, the provider can select the procedure code selection graphical interface 108 so that the procedure code selection display subsequent in hierarchy to the new bill graphical display is generated. The procedure code selection display including: an open text field for receiving procedure code related information; and a results display for displaying a plurality of procedure codes returned as results based upon the procedure code related information. The provider can use the procedure code selection to add the procedure information and the associated CPT billing code in the same manner, by speaking or selecting the appropriate procedure. If the returned procedures are incorrect, the doctor can initiate the verbal billing search again without selecting a result from the list of billing codes returned in the last verbal billing code query. When the correct code is returned, it can be selected. Once the doctor is satisfied with the face sheet image quality after the provider's human quality assurance review, the approved image is then appended to the bill. If a doctor wants to add a memo, this also can be done verbally. For example, the doctor can speak "biller, please make sure we have captured the appropriate charges for the ankle splint that was provided to the patient period." The doctor then approves and saves the memo.

The next step is review of the bill information. The date of service is defaulted to today by the app. The date of admission can be added to the bill. The name of the doctor currently logged in is added. If the software user is billing for someone else, another doctor can be selected. The name of the facility can be added. The name of the referring doctor can be added. Once the user has entered the referring provider, the referring provider goes into the user's list of providers that are referring the user patients.

At this point the user is done and the user can hit submit. That bill goes into the user's bill history. The charge just created with its annotations, including images actually uploads in the background. The new charge is flagged as a new charge in the user interface. All charge data, including images, is securely transmitted and processed—structured data deriving from the patient information in the image submitted is created. the billing information is sent to the charge capture manager device 20.

After entry of information by the doctor, the biller is notified that there are new charges. The biller logs into the system (charge database in memory 2006 on the charge capture manager device 20) via a web browser on a client device 10 and can see the charge the provider just created for 'jane doe.' The image derived patient demographics have been generated and the user can search, sort and filter the charges that users in the account have submitted based on the patient demographics and/or other information captured. The record from the list of submitted charges in the account provides a detail view of all of the information provided by the provider, including the transcript that was created by the provider for the billing staff. The billing staff has the opportunity to filter the bills based on status, and can change the status of the bills, can change what information is displayed and they can filter by user.

Thus, by using the invention, a doctor can improve workflow, capture more revenue and obtain payment faster by automating steps in the revenue cycle and eliminating inefficiencies, interim steps, and delays in information gathering (from multiple sources and physical locations) and submission. The invention accomplishes this by enabling on-the-go healthcare providers to capture and submit information about services rendered from any location via multiple modalities available on a mobile client device. By using the technology, health care providers and healthcare provider organizations can accelerate clinical and administrative workflows, leading to more streamlined and timely medical claim generation and submission.

The system permits the collection of data utilizing multiple peripherals on a mobile client device 10 (including, but not limited to the microphone, accelerometer, video sensor, global positioning system, touch screen, keyboard) or peripherals that may be tethered to a mobile client device 10 or wirelessly communicate with a mobile client device 10 (i.e., a signal from another piece of electronic equipment) or utilizing the mobile client device's ability to communicate (wirelessly or via wired connection) with an in house or third party information system. One potential application of the system is to collect data that documents and memorializes the occurrence of a billable medical encounter or episode of care between a provider and a patient or a billable service including but not limited the interpretation of a diagnostic study or review of the results from a diagnostic study. The system safely manages data that may contain personally identifiable health information that needs to be managed consistent with the HIPAA security and privacy rules and regulations Data Collection The data collected may be any combination of a multitude of types including, but not limited to:
  All or a subset of the information that is necessary to collect for the purpose of activities including but not limited to: billing for medical services or procedures, assembling a medical claim, documenting the performance of medical services or procedures, preparing a report for presentation internally, to a third party, or to a patient, for record keeping and compliance purposes, for accreditation, for executing safety surveillance or quality improvement efforts, for participation in medical research or pharmaceutical post marketing surveillance;
  Image based data that may contain written (handwritten or typescript) text or language that originated from a hard copy (i.e., a physical print out on a piece of paper) or a soft copy (i.e., an image rendered on a computer screen). For example, text data that might appear in clinical charting, diagnostic study reports, patient registration and insurance data, patient identification, legal contracts (i.e., advanced directives, procedure consent forms), questionnaires or feedback data provided by a person (i.e., a patient or a consultant);
  Image based data that is the output of some diagnostic procedure such as a radiograph (including, but not limited to one or a collection of plain film x-rays, computed tomography scans, magnetic resonance imaging scans, electrocardiograms, electroencephalograms, nuclear medicine studies, read outs rendered on the screen of various monitoring devices or a hardcopy thereof, data plotted on axes of some sort to demonstrate trends such as for example the change in the value of a vital sign over time, soft or hard copy reports and images from machines that may analyze a specimen originating from a patient (i.e., cluster of differentiation based immunophenotyping) or the amplification of a specimen from a patient (an example of the latter being a polymerase chain reaction and gel electrophoresis);

Image based data of a person, group of persons, or a particular part of a person or their anatomy or the condition thereof, including but not limited to an intraoperative image of a surgical site either with or without magnification (i.e., an image from an intraoperative microscope), image of a catheter, tube or line in place on a patient, image of a post-operative wound, image of a skin condition, image of a specimen (i.e., a surgical biopsy) either in gross or under low or high-power magnification such as that of an light microscope or electron microscope with or without staining, immunohistochemistry, immunofluorescence, etc.;

Verbal, or text data created generated by the end user of the technology (i.e., by using voice to text, handwriting, typing, searching a database of data on the client device 10, at the manager device 20 or another remote device and selecting items from the results to be added as annotations to the data being collected such as for example a medical diagnosis, evaluation and management, or procedure code);

Actively entered data (for example, information a user may provide by typing it into a form, by speaking, by interacting with and providing data via a software user interface via touch, voice or gestures) or passively collected data that the user has opted into providing or that the user is authorized to collect (i.e., the recording of a conversation, the users location as provided by global positioning system, the users movement such as that which may be provided by an accelerometer, etc.); and Information that is pulled from an information system that the user is authorized to access, that the user's mobile client device 10 is authorized to access and that the user's mobile client device 10 is able to connect to via a wired or non-wired connection. Examples may be accessing and pulling in patient or provider data from a hospital, a payor, a third party vendor system (i.e., credit scoring service, insurance validation service, etc.), pharmaceutical company database, a research database, an ontology database such as for example a database containing SNOMED data, using key words or search terms, or using record locators or identifiers captured by the mobile device's video sensor, captured by manual data entry (i.e., by typing or voice) by an end user, captured using physical characteristic or biometric data (i.e., image of an individual's face, a finger print, a retinal scan, using deoxyribonucleic acid, a protein sample, or analysis thereof).

The data captured via the various modalities can be temporarily securely stored on the mobile client device 10 or transmitted, immediately or at a later date decided by the user or based on programmatic instructions, via a wired or non-wired connection in a secure fashion consistent with any organizational policies, HIPAA, or any other privacy or security laws.

The data may be transmitted securely to a server residing in a data center or another location. The server can provide the charge capture manager device 20. The data is securely managed by commercially reasonable means both in transmission and at rest in a fashion consistent with organizational policies, HIPAA, or any other privacy or security laws.

The data collected or a summary or subset thereof may at some point be transmitted securely to populate a third party system via an API or via a standard messaging protocol, including but not limited to Health Level Seven—HL7 messaging. An example of this might be transmission of the data to a practice management software being used to prepare claims to bill a payor for a medical service or procedure or transmission to a claims clearing house, in the case where the data has been organized and assembled into a medical claim.

Figure 27:
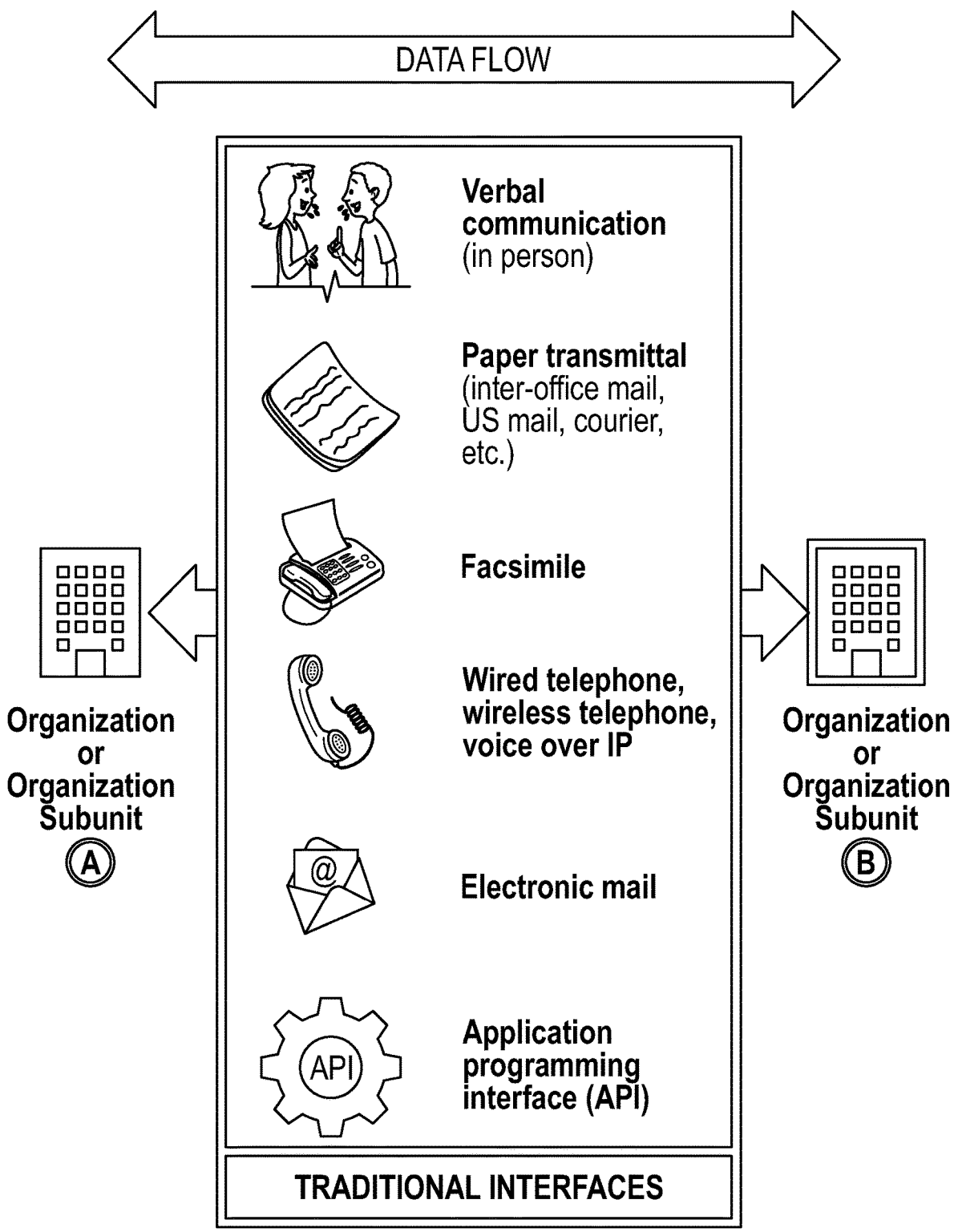
FIG. 27 depicts more traditional interfaces for data exchange between organizations or within organizations.

The data can be organized, annotated, processed, analyzed, and synthesized throughout the process (i.e., during collection or after transmission, etc.). Feedback may be provided to the user about the data initiated by a machine driven by logic or feedback from a remote party interpreting or reviewing the data during or after its collection. Feedback might include but would not be limited to feedback on the quality of the data or the completeness of the data (i.e., notification about missing or outstanding data that still needs to be collected), conclusions determined and arrived at via analysis of the data collected and some other logic (business rules, clinical decision support, or any other algorithms), and/or suggestions about next steps that should be taken. Feedback may be delivered by a multitude of modalities via the mobile device including tactile, audio (speaker), visual (user interface) or other means A Data Transmission Interface As shown in FIG. 27, traditional means of data exchange or interfaces between organizations consist of in person verbal communication, wired telephone and facsimile communication, paper based communication (i.e., mail or courier service), or email communication, text messaging, an application programming interface, among others.

One of the manners in which the inventive system described can be employed is as a means or interface between two organizations that need to securely transfer information including protected health information driven by a human or machine actor using a mobile device. The data transfer may be necessary for any authorized need including but not limited to a business need (i.e., medical billing and medical claims preparation), a compliance need, a quality monitoring need, an accreditation reporting need, a research need, and other needs. The current invention describes a new data exchange interface driven by an authorized human or machine actor using mobile technology whereby the actor can collect data from multiple data sources utilizing the mobile device and its peripherals.

Data may be actively captured or passively captured. Data may include, but is not limited to, data collected from manual data entry, from verbal data, from global positioning system data that may or may not be correlated with an action of the actor, from the current time (i.e., the actor's location where and time when a particular action was carried out or the location and time at which a particular event occurred), from images, such as, for example, snapshots of textual, graphical or pictorial data that is on a hard copy medium like paper, snapshots of similar information that is presented on a graphical user interface of some sort like a computer or workstation monitor, snapshots of a person, a part of a person, or a pathology of interest, snapshots of analytical readouts from specimens obtained from a patient or images of the patient specimen(s) under magnification with or without special dying or immunohistochemical staining, and/or snapshots of imaging studies (i.e. diagnostic imaging studies) that may be presented on a physical printout or as an image rendered on a computer or picture archival communications system (PACS) workstation).

Data may be collected at any location in one sitting, session, or episode or over a series of sessions, sittings, or episodes. Data collection locations might including but are not limited to, an office or business location, a residence, a skilled nursing facility, an acute care hospital, a rehabilitation hospital, an ambulatory surgery center, an outpatient clinic, a motor vehicle, a mobile clinic, a retail location, or other location.

Data may be collected by one individual or machine actor or collaboratively by multiple individuals and/or machine actors using mobile devices. Individuals may include, but are not limited to be employees of an organization, business associates and contractors of an organization, customers or patients of an organization, medical providers, among others.

Data is collected, annotated, assembled/organized, analyzed, processed, and submitted using various gestures (i.e., touch gestures) or verbal commands.

Figure 28A:
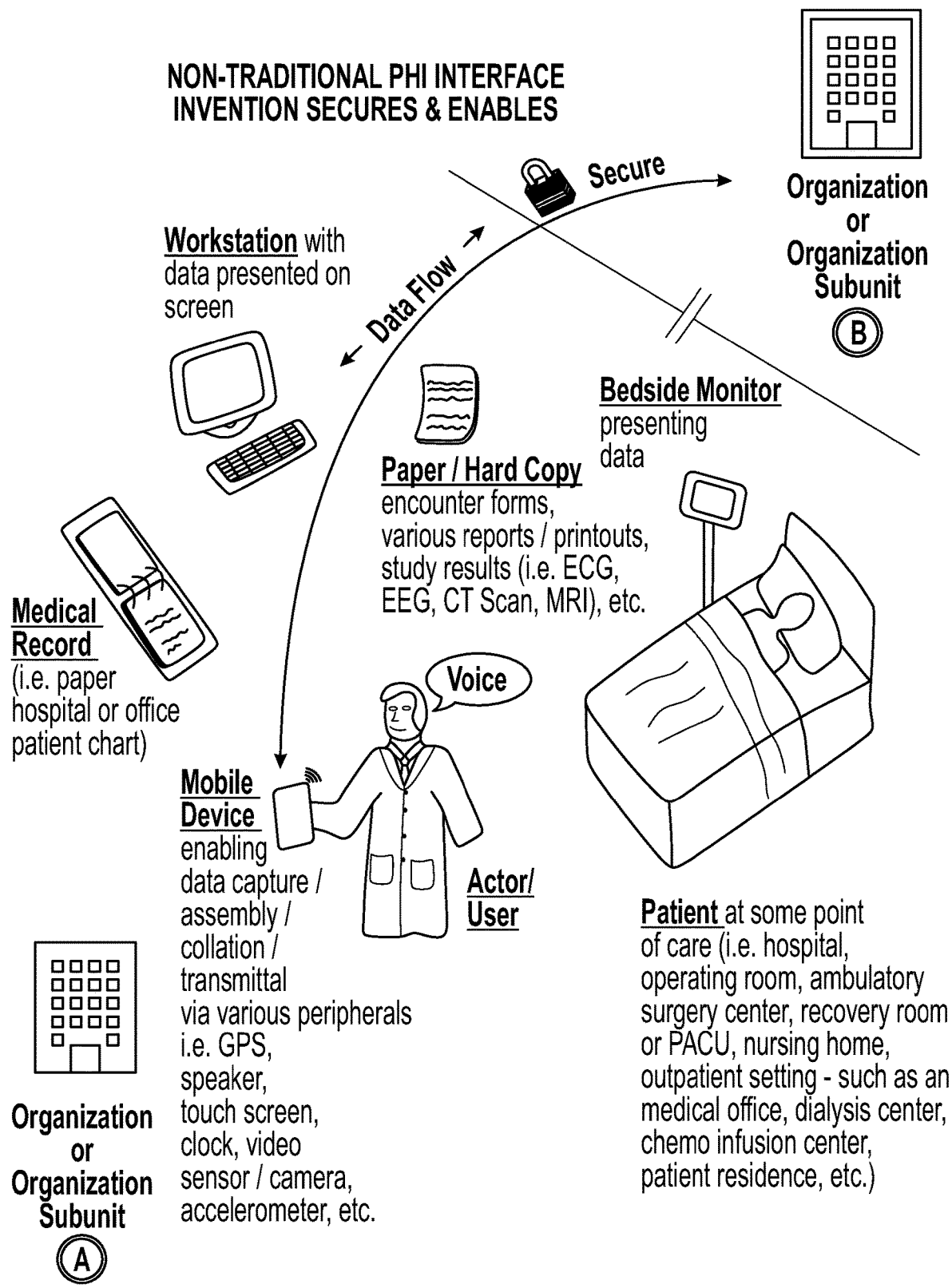
FIG. 28A depicts an application of the present invention in a medical context where a mobile provider is using his or her mobile device at some point of care (i.e., a hospital) and in the course of his or her activity is capturing data necessary to document, bill for, and memorialize the services or procedures rendered for one or more patients.
Figure 28B:
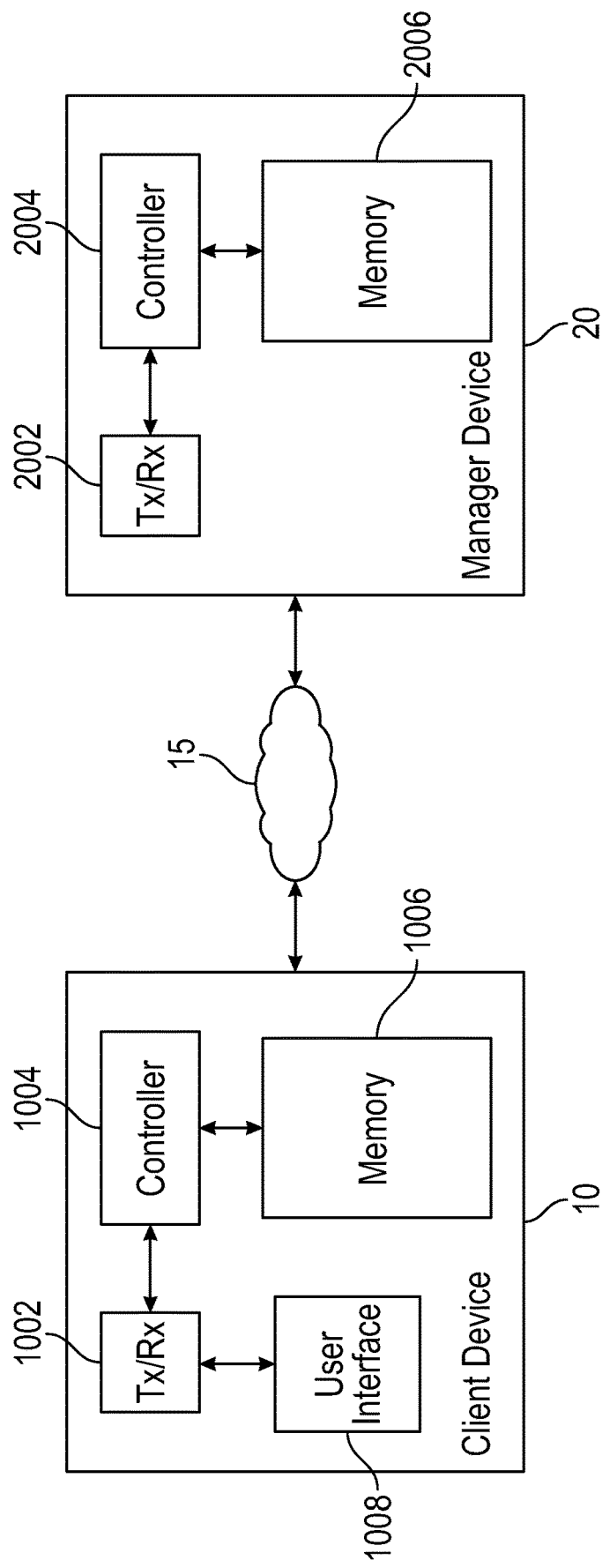
FIG. 28B is a block diagram illustrating exemplary portions of the client device and manager device at the organization in an exemplary operating environment.

FIGS. 28A-28B depict an application of the present invention in a medical context where a medical service provider is using his or her mobile client device 10 at some point of care (i.e., a hospital) and in the course of his or her activity is capturing data necessary to document, bill for, and memorialize the services or procedures rendered for one or more patients. The mobile client device 10 is equipped with multiple peripherals that enable data collection of numerous types, both passive (i.e., GPS position and event time) and active (snapshot images taken with the video sensor or data keyed in or added verbally as annotations to data collected). The actor (mobile healthcare provider) can utilize the video sensor on the device 10 to capture textual, graphical or pictorial data that may appear on a piece of paper (i.e., a hospital form or report like a 'patient sticker' or a patient 'face sheet' with patient identifiers and patient insurance information needed to bill the services), that may be in the form of a note that the healthcare provider hand wrote or typed and placed in the patient's paper or electronic medical record 'chart', that may be in the form of a snapshot of a patient, a wristband the patient may be wearing with personal identifiers and record locators, a part of the patient (face, surgical wound, site with a pathology that is being managed by the medical provider), or the patient in the midst of a procedure (i.e., an intraoperative image or snap shot of a fluoroscopic intra-procedure image that documents some aspect of the care—such as the procedure being done at a particular and correct anatomical site), that may be in the form of a diagnostic imaging or other study being reviewed on a workstation monitor or a hard copy on a light box (i.e., a film showing a particular finding on an imaging study). The actor may also annotate the images and other data with manual data entered into the mobile client device 10 by voice, by typing on the device keyboard or by interacting with the software (stored in the memory 1006) on the mobile device 10 via the touch screen (i.e., adding some details of the services provided, adding a memo to be reviewed by a staff member or medical biller in the back office, searching for appropriate codes and then adding or annotating the data set with the diagnostic or procedure codes for the services provided). The invention allows the actor to use their own mobile device or an employer issued mobile device to collect, assemble, annotate and subsequently transmit this data (via transceiver 1002) to a data center (charge capture manager device 20) in a remote location where the information will be used by other actors or machines to execute downstream business processes. The invention provides a means for securely managing (collecting, persisting, transmitting) the data set collected which, in this example would include personal health information and patient identifiers that need to be protected and managed securely by law.

Figure 8:
Figure 9:
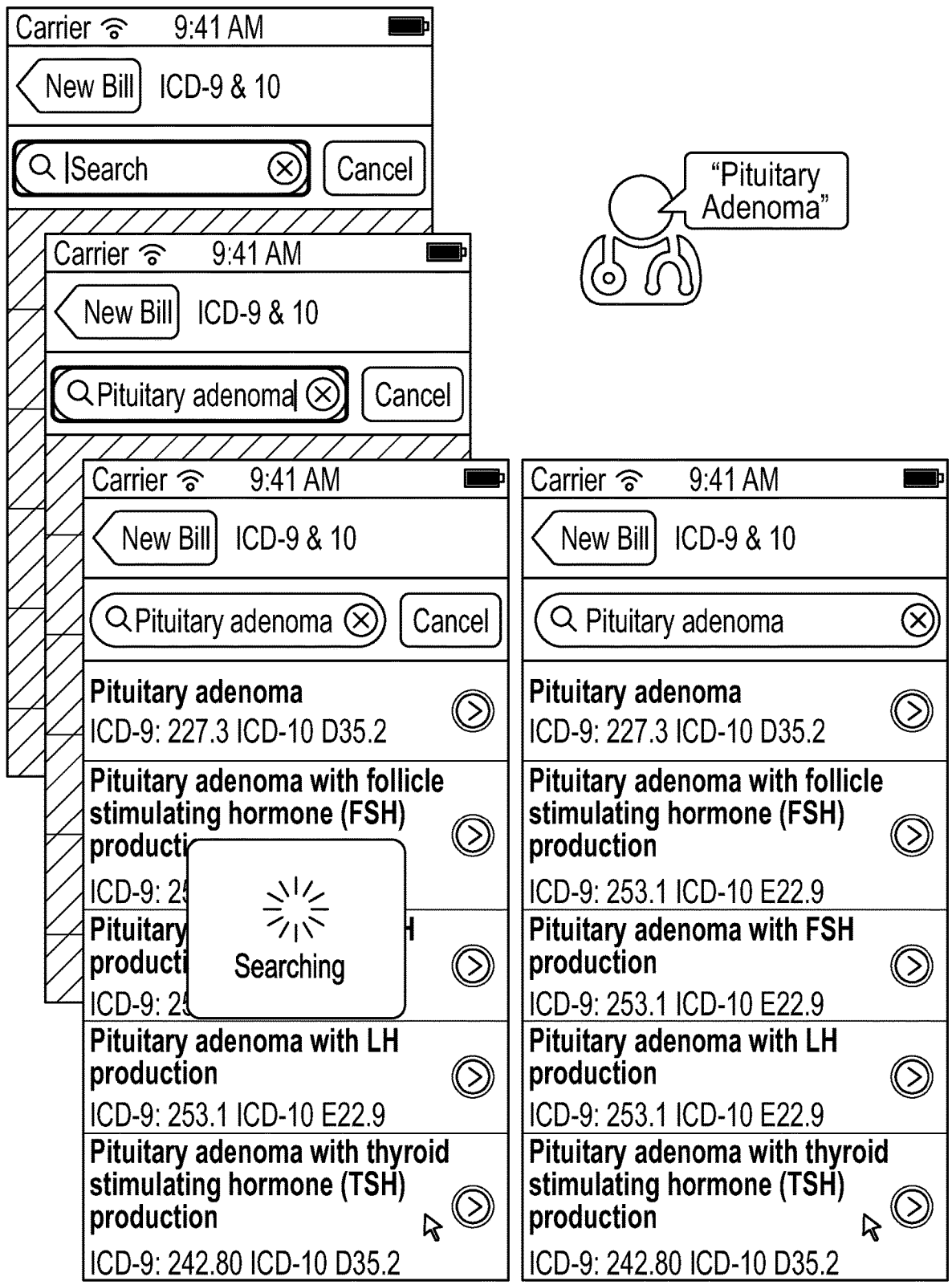
Figure 10:
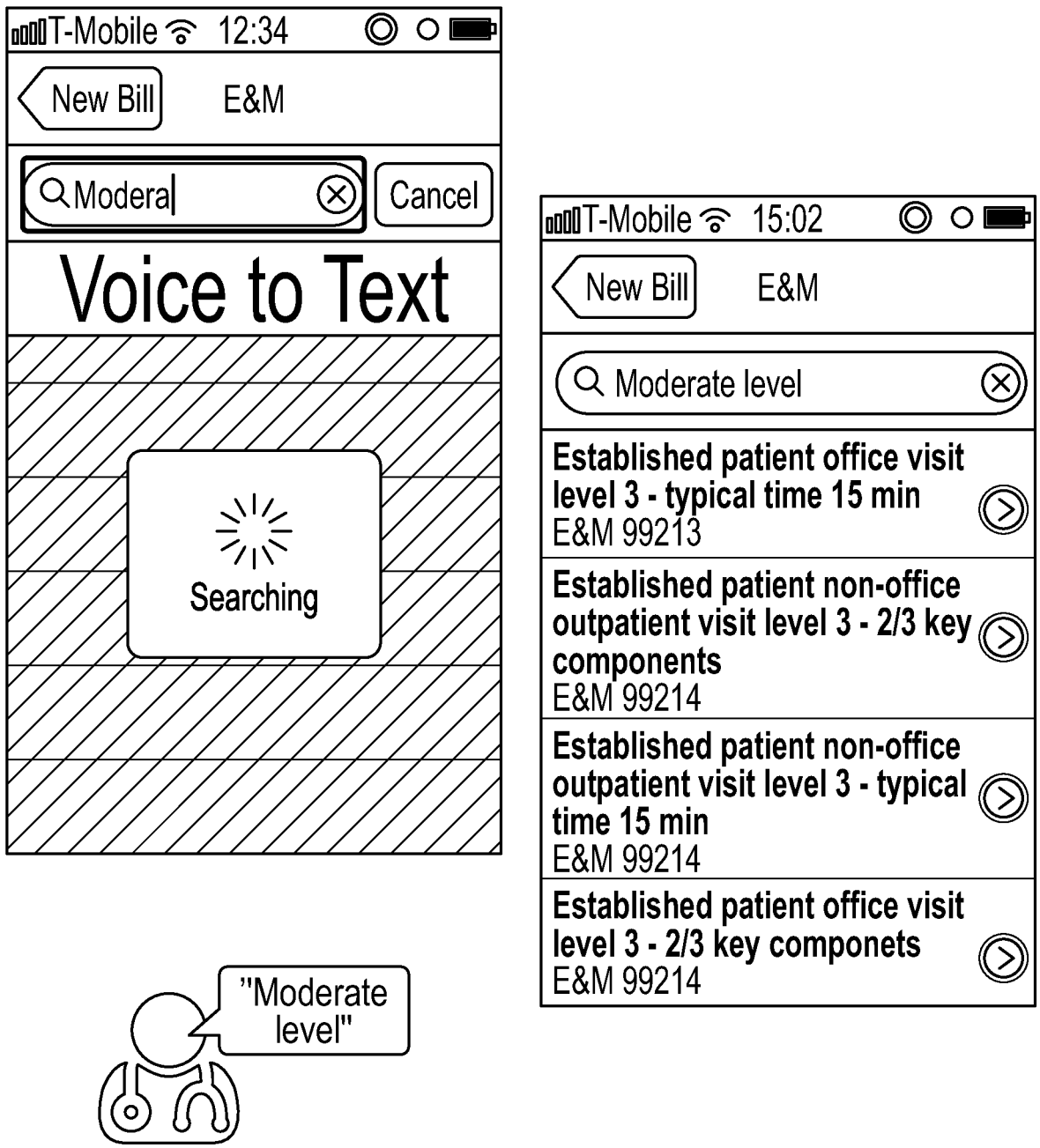
Figure 11:
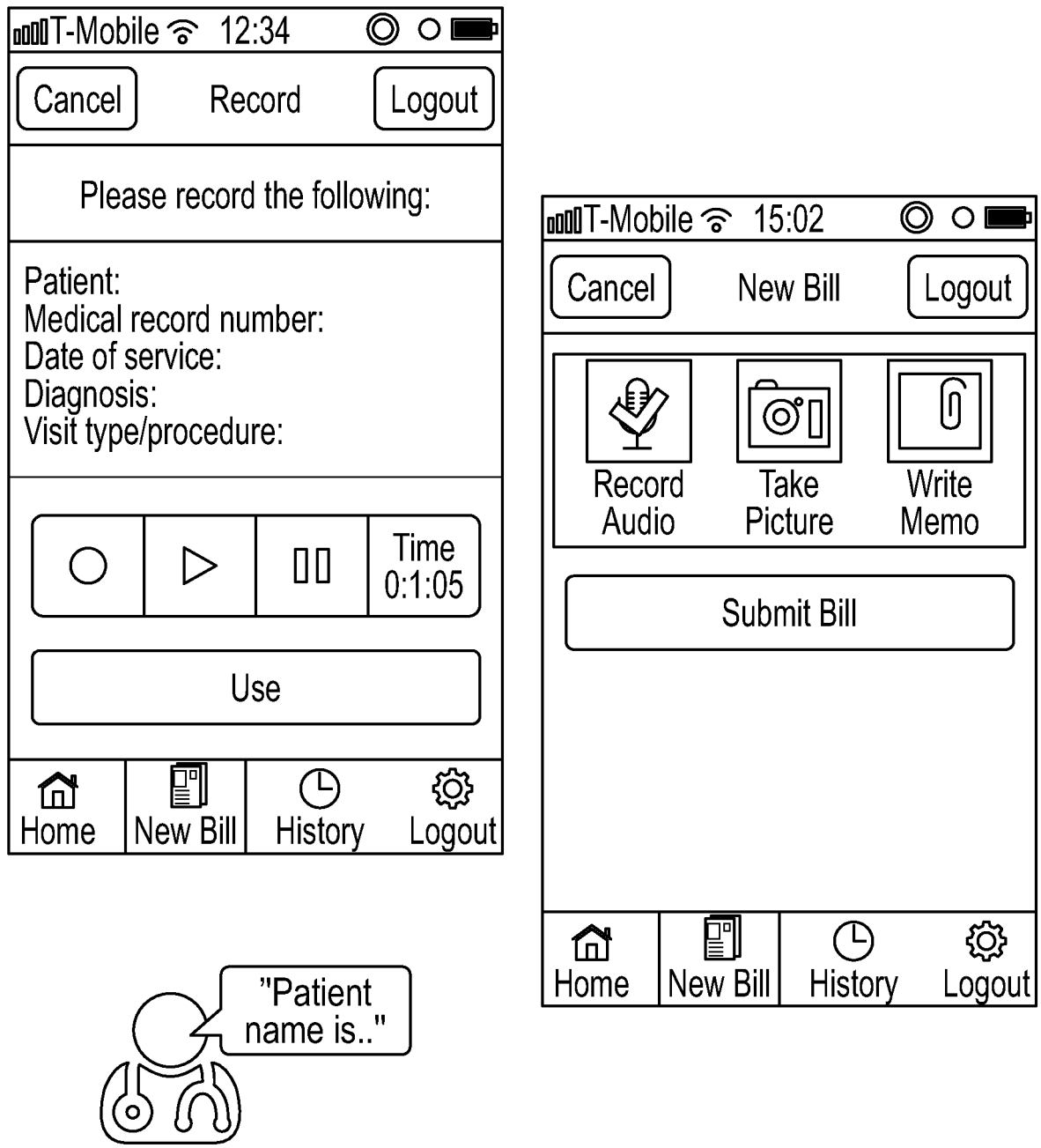
Figure 12:
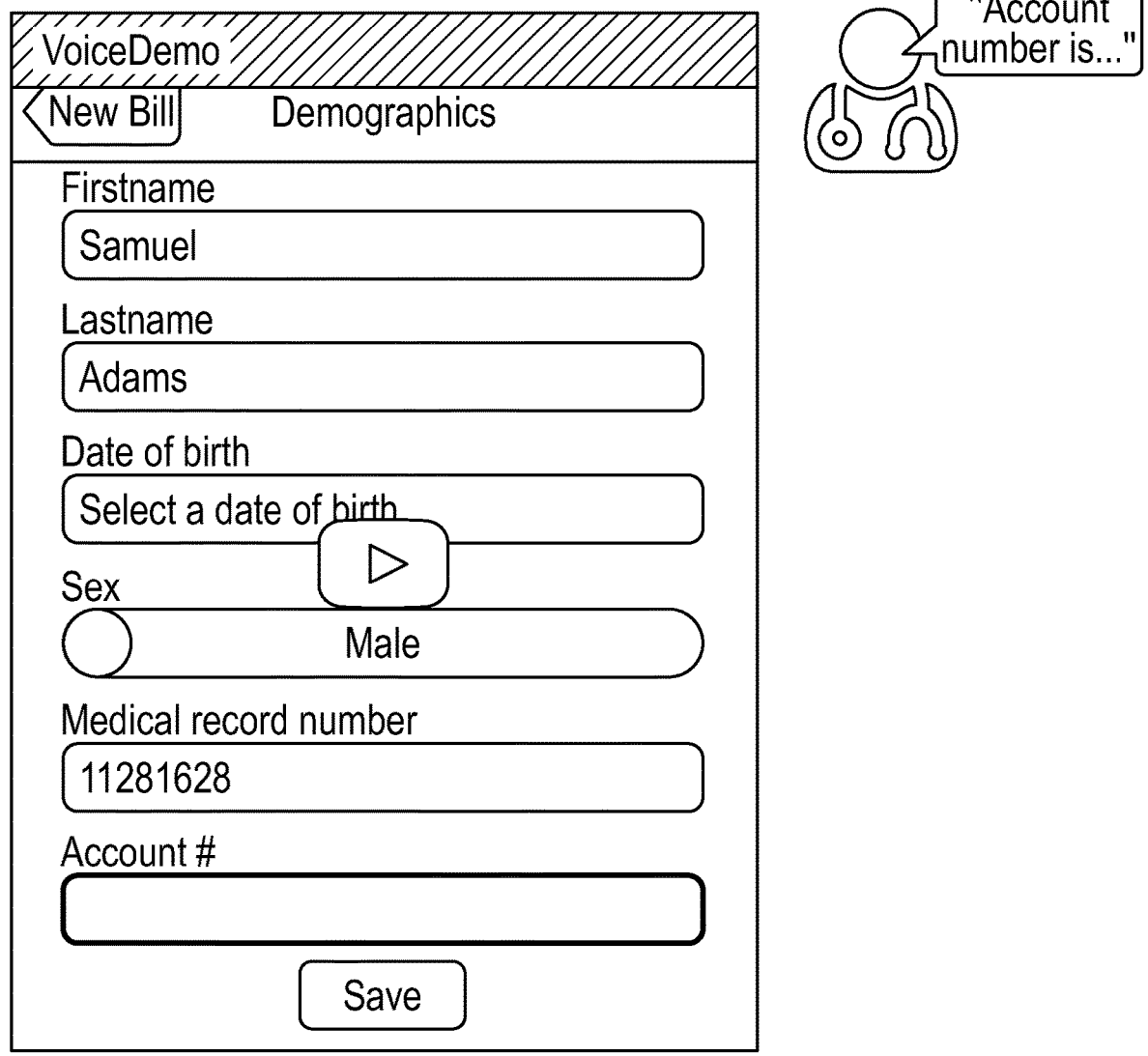
Figure 13:
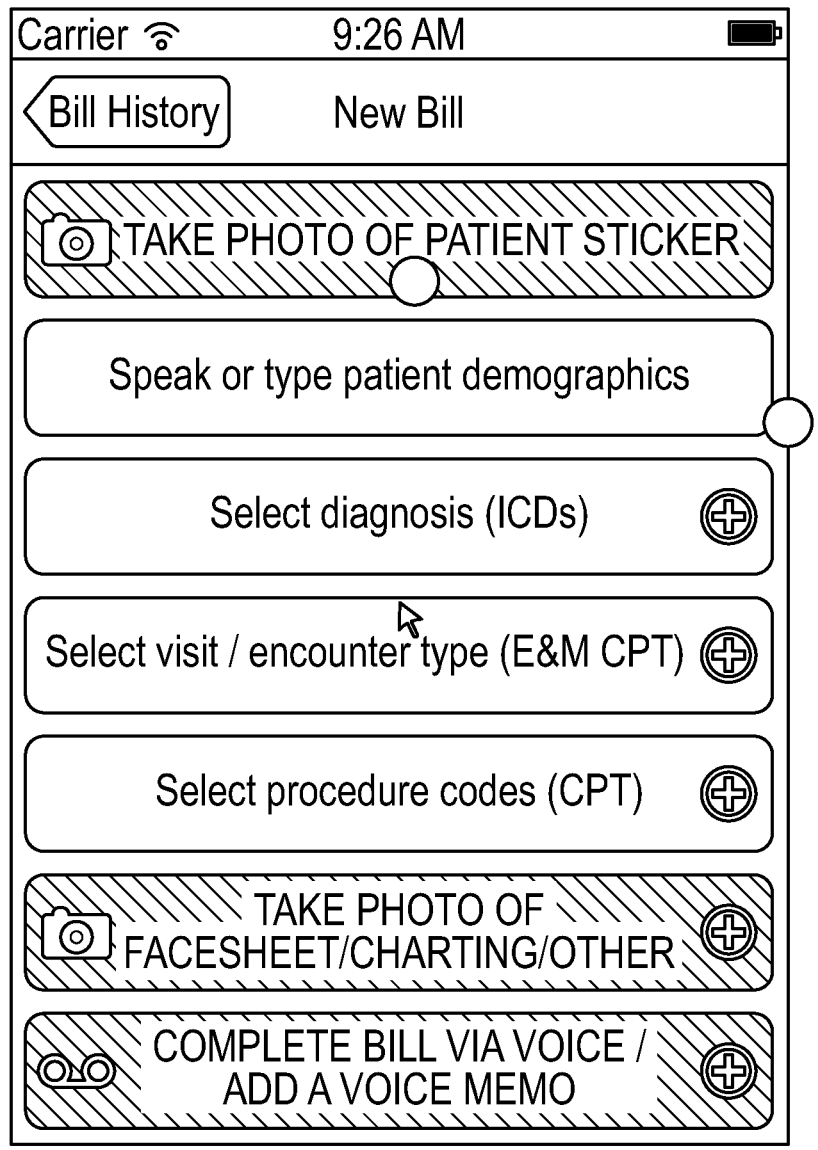
Figure 14:
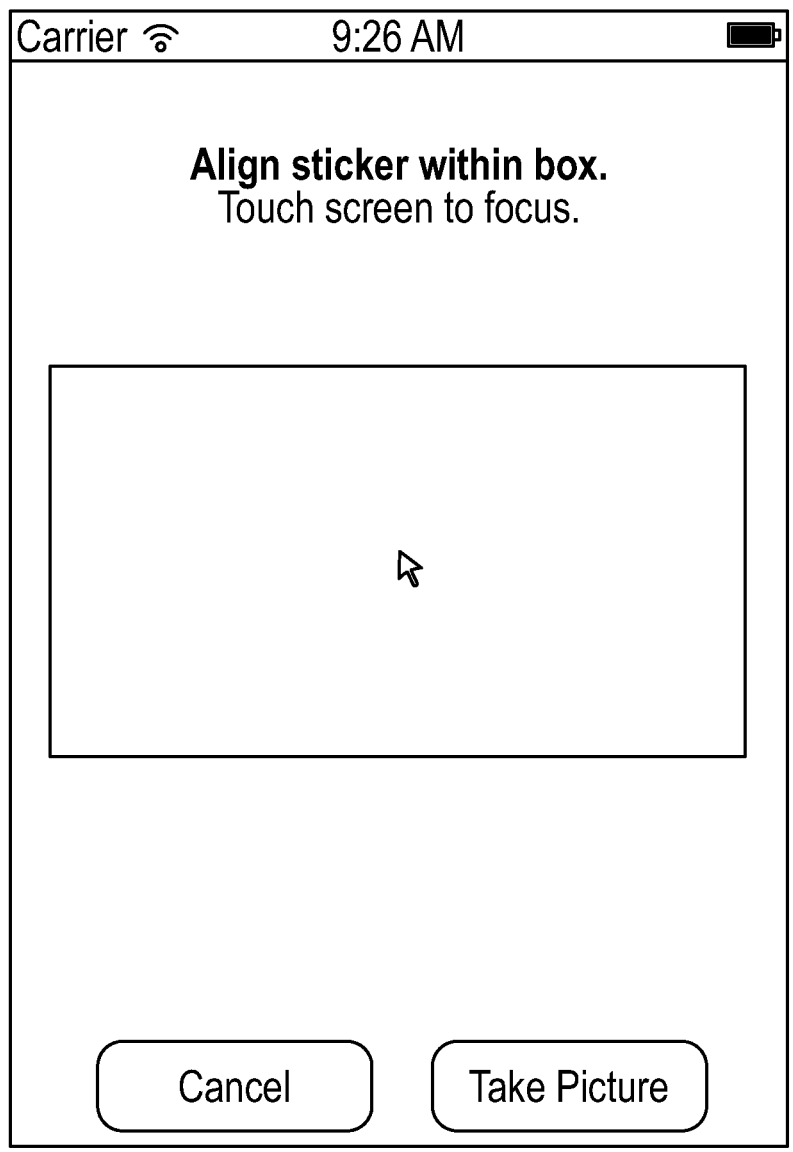
Figure 15:
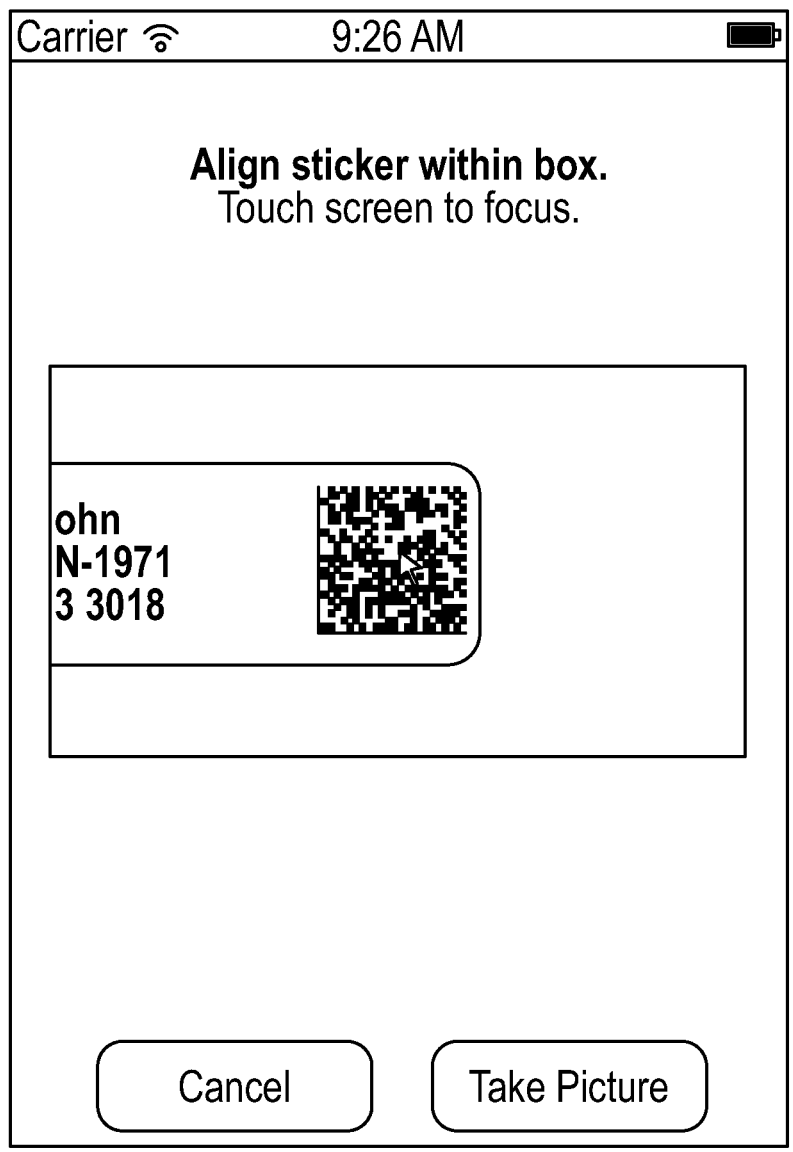
Figure 16:
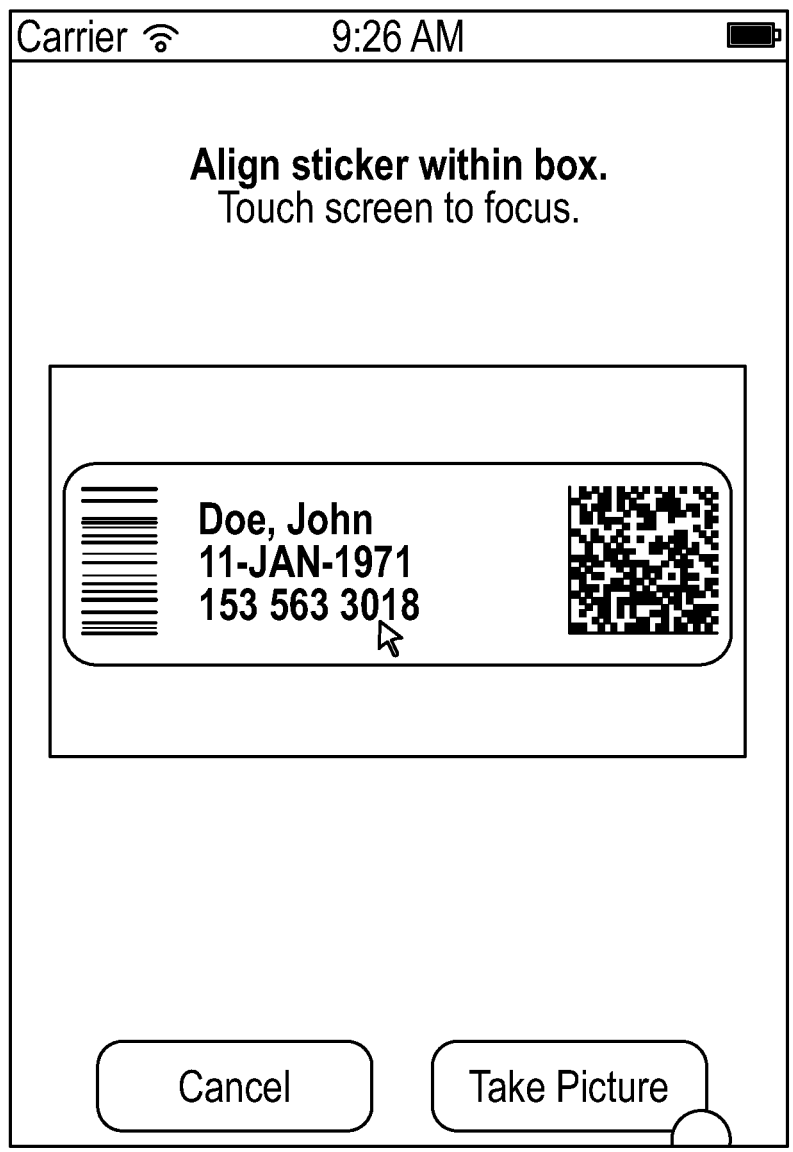
Figure 17:
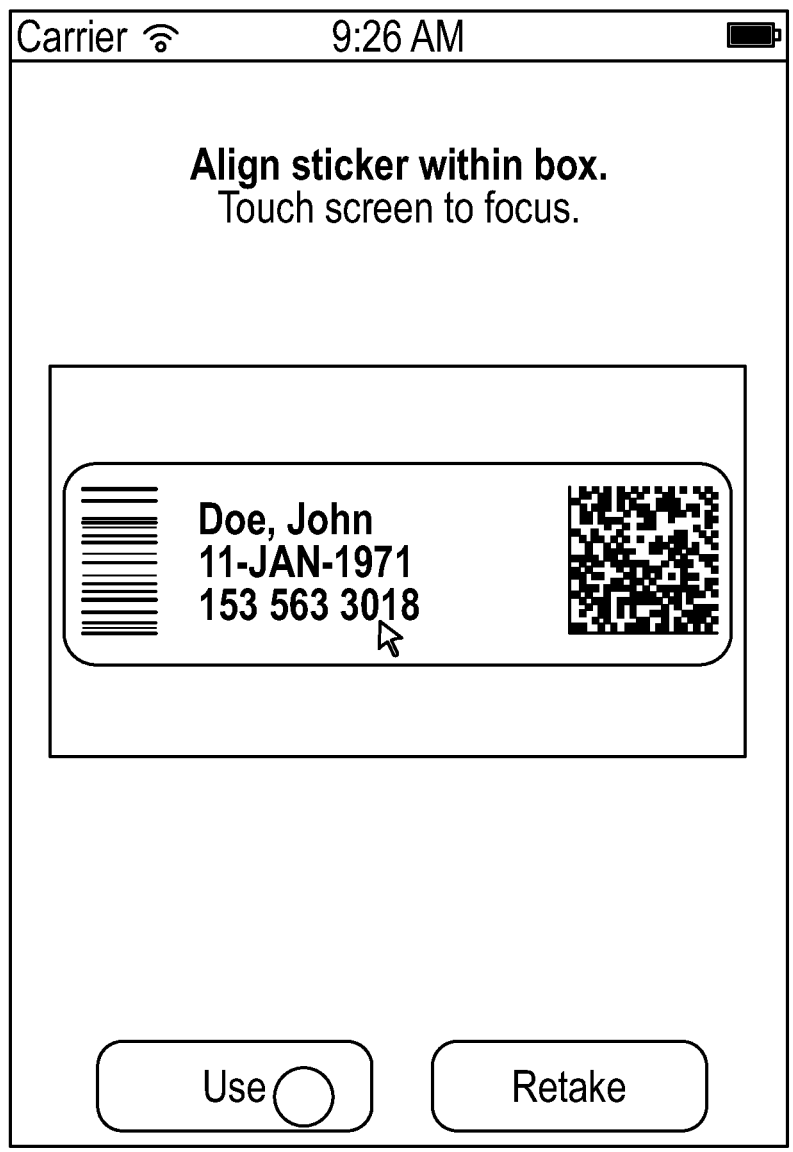
Figure 18:
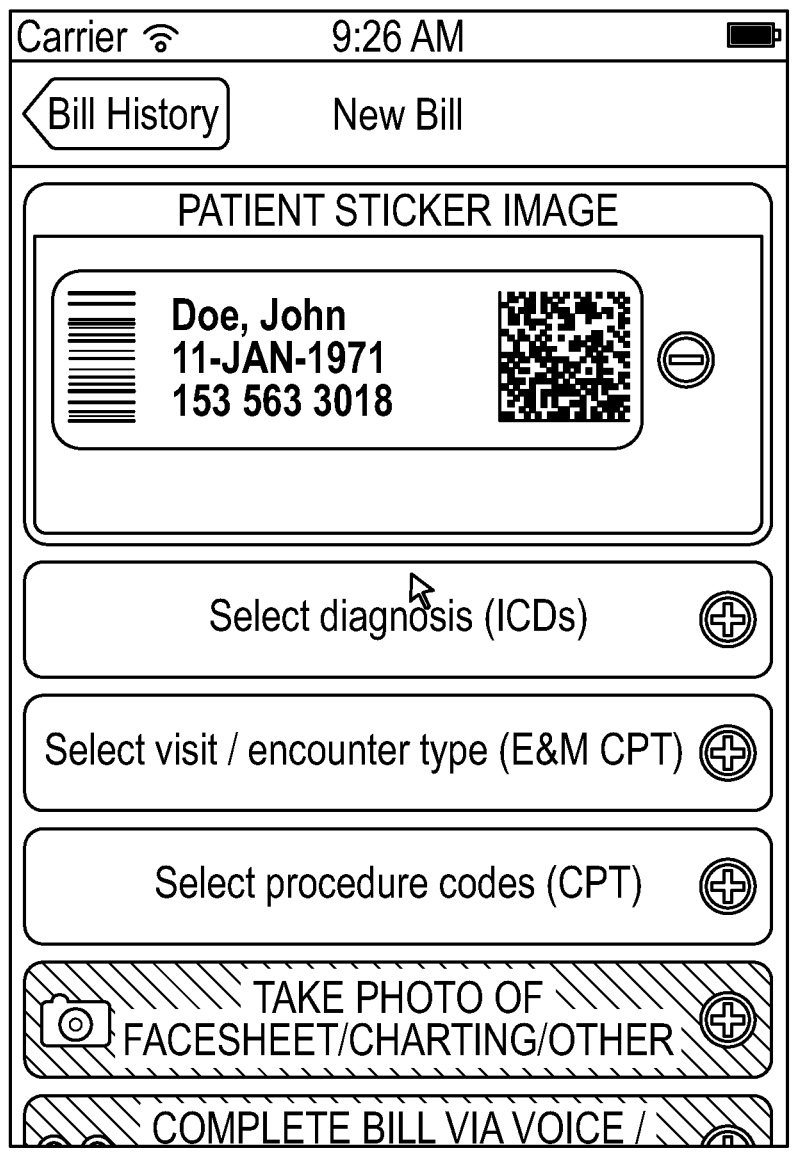
Figure 19:
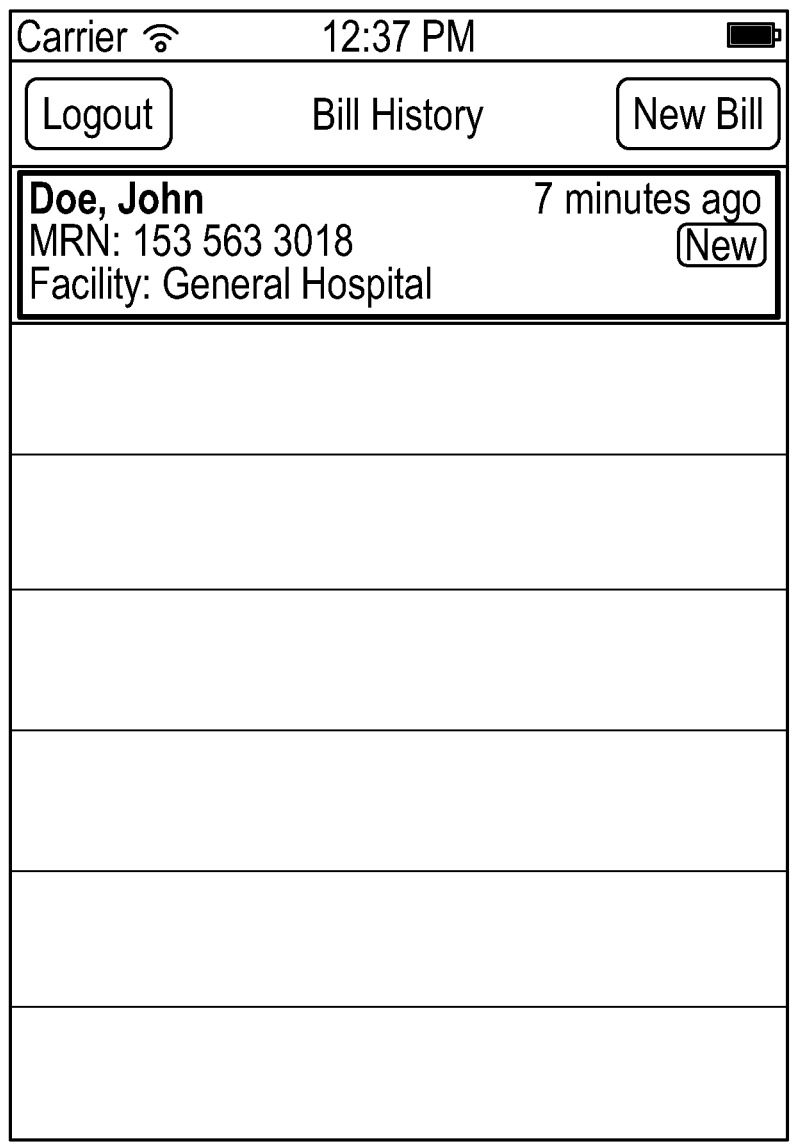
Figure 22:
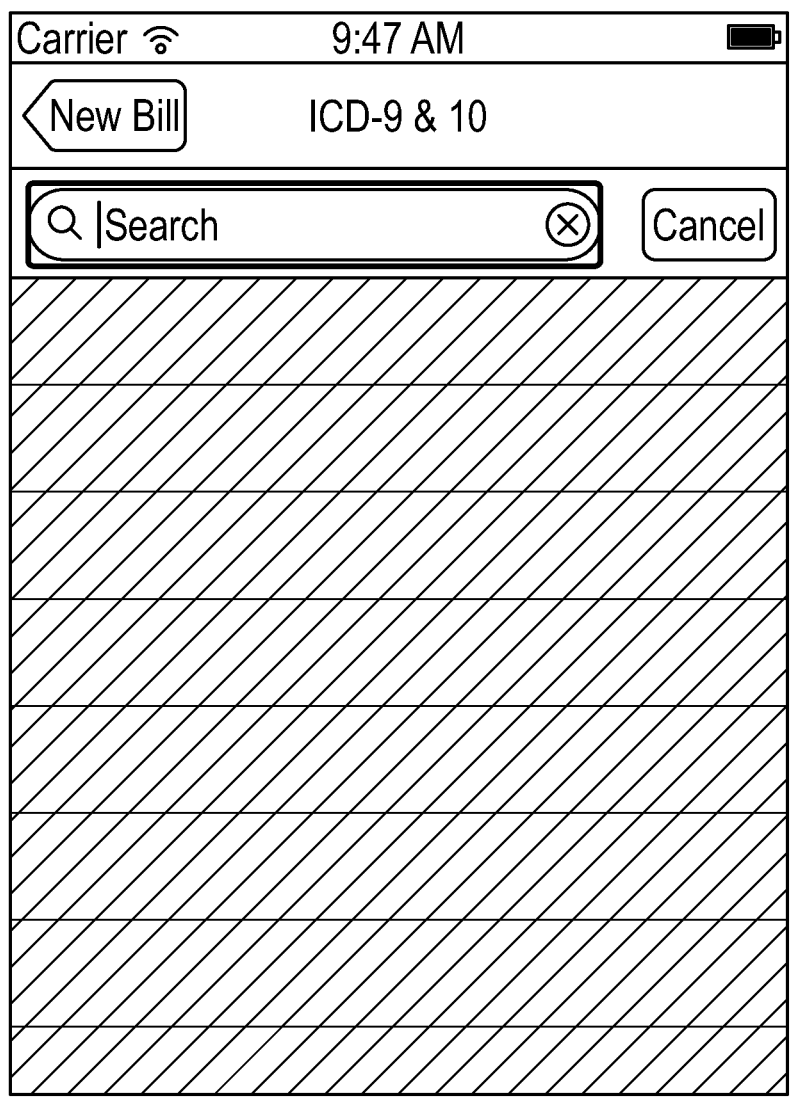
Figure 23:
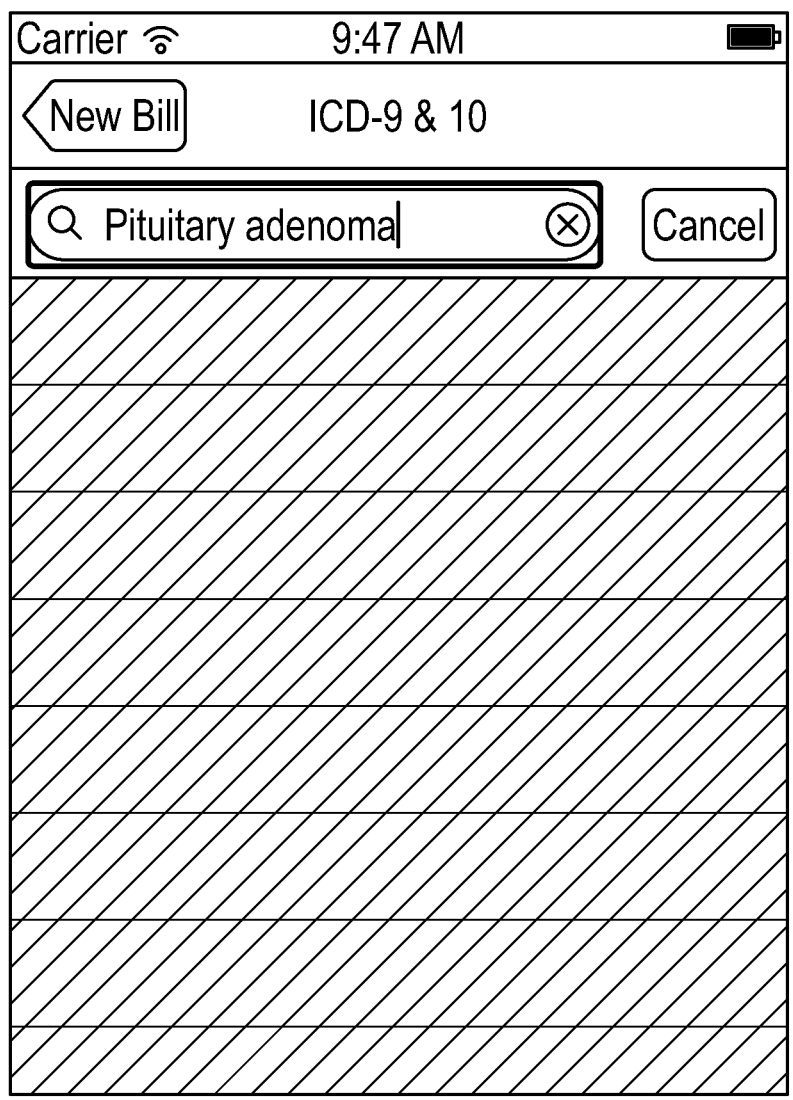
Figure 24:
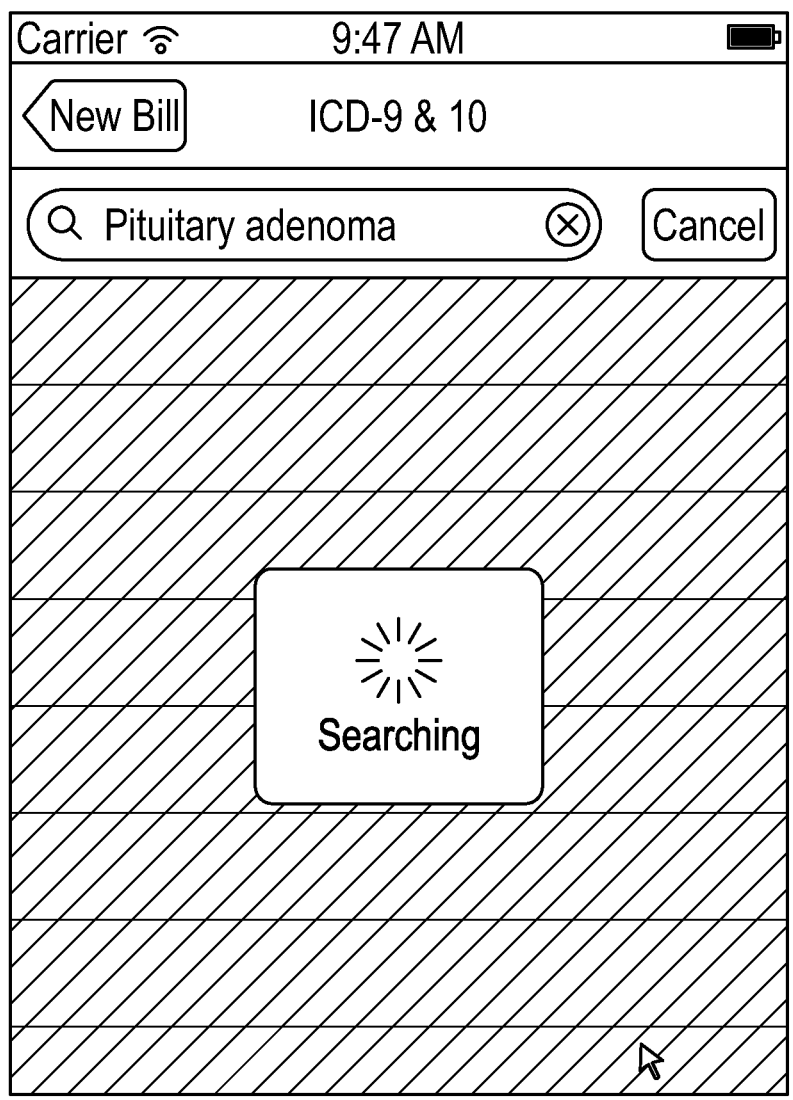
Figure 25:
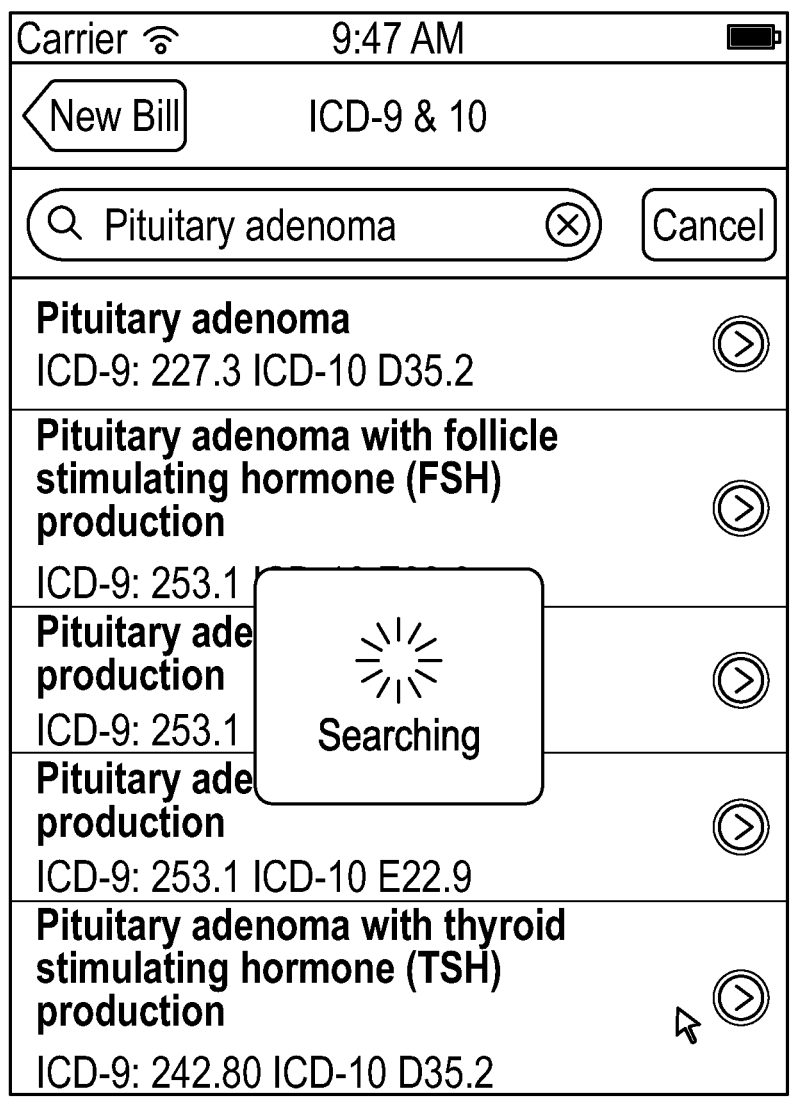
Figure 26:
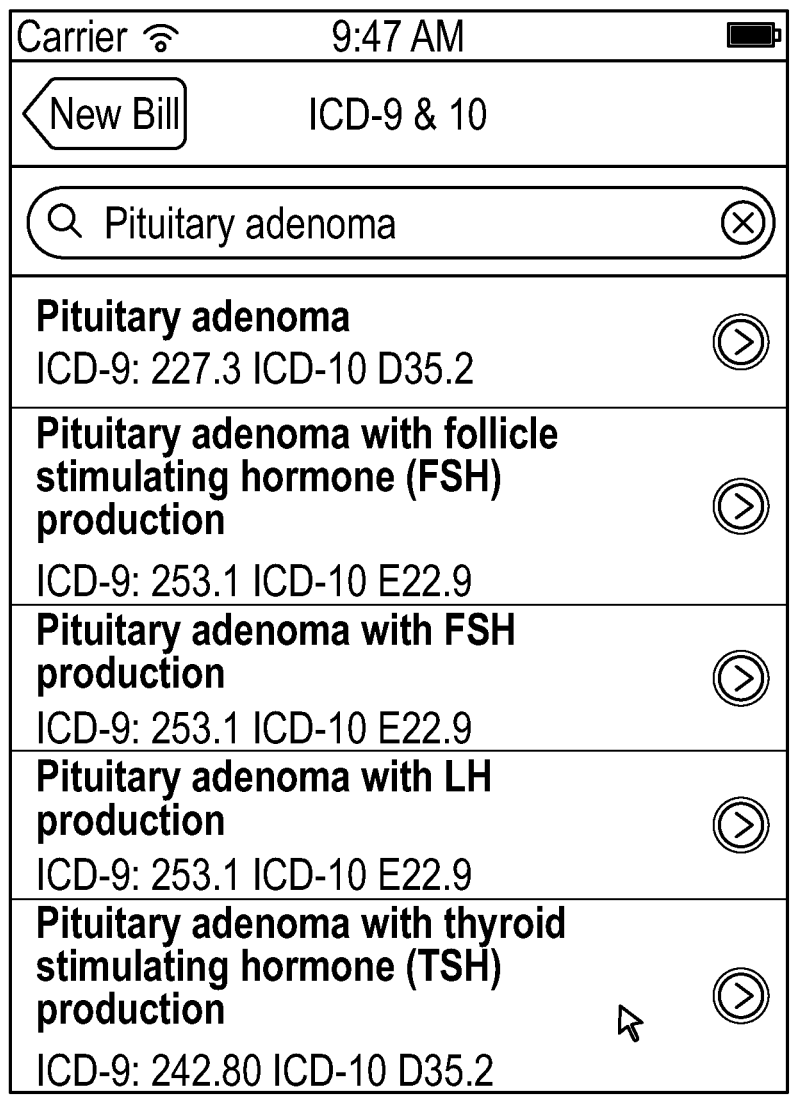

The charge capture manager device 20 in the remote location includes a transceiver 2002 configured to receive a resource request from the client device 20. The resource request includes authentication credentials associated with a user name. The manager device 20 includes a controller 2004 operatively coupled to the transceiver 2002 and one or more memory sources (depicted by 2006) operatively coupled to the controller 2004. The one or more memory sources 2006 include a charge database and instructions for configuring the controller 2004. The instructions configure the controller 2004 to add a new bill data set received from the client device to a bill history and set a status flag associated with the data set to indicate new charge, the new bill data set including patient identification information, one or more diagnoses, one or more one or more evaluation and management codes, a procedure billing code, date information and user information in the data set. The instructions configure the controller 2004 to generate an acknowledgment message indicating successful transmission of the new bill data set to be sent to the remote client device 10; delete a data set indicated in a request from the client device 10, generate a notification message to be sent to another remote client device such as the biller indicating that the new bill data set has been stored; modify the status flag associated with the data set in response to a resource request received from the another remote client device including a request to change the status flag as shown in FIG. 8; and maintain an activity log of all access to a data set in the charge database.

The controller 2004 can be further configured to determine the bill history in the charge database that is associated with the user name to be sent to the remote client device 10 during the secure communication session by the transceiver 2002, the bill history including one or more data sets, each of the one or more data sets including a patient identification of a patient for which a bill has been created, a medical record number and facility, date information regarding when a charge was submitted, and a current status of the charge.

The foregoing detailed description of the preferred embodiments has been presented only for illustrative and descriptive purposes and is not intended to be exhaustive or to limit the scope and spirit of the invention. The embodiments were selected and described to best explain the principles of the invention and its practical applications. One of ordinary skill in the art will recognize that many variations can be made to the invention disclosed in this specification without departing from the scope and spirit of the invention.

What is claimed is:

1. A charge capture client device comprising:
   a transceiver for communicating with a charge capture manager device via a connection to a network;
   a controller coupled to the transceiver; and
   a memory coupled to the controller, the memory including instructions to configure the controller to:
      generate a new bill graphical display for facilitating user entry of a new patient data set, the new bill graphical display including:
         an image graphical interface, wherein an image input interface is generated when the image graphical interface is selected for receiving an image including patient identification information so that the patient identification information can be extracted from the image;

a voice input graphical interface, wherein a voice input display subsequent in hierarchy to the new bill graphical display is generated when the voice input graphical interface is selected, the voice input display including:
  a record control graphical interface for recording voice utterances including patient identification information when selected;
  a transcript display portion for displaying a transcript of the voice utterances; and
  a plurality of template graphical interfaces for categorizing information included in the voice utterances to extract the patient identification information;

a diagnosis selection graphical interface, wherein a diagnosis selection display is generated when the diagnosis selection graphical interface is selected, the diagnosis selection display subsequent in hierarchy to the new bill graphical display, the diagnosis selection display including:
  an open text field for receiving diagnosis related information;
  a results display for displaying a plurality of diagnosis codes returned as results based upon the diagnosis related information; and
  a favorites display for returning a plurality of diagnosis codes selected more than a predetermined number of times in a predetermined previous time period or diagnosis codes previously designated as favorite diagnosis codes;

an evaluation and management (E/M) code selection graphical interface; and a procedure code selection graphical interface, wherein a procedure code selection display is generated when the procedure code selection graphical interface is selected, the procedure code selection display subsequent in hierarchy to the new bill graphical display, the procedure code selection display including:
  an open text field for receiving procedure code related information; and
  a results display for displaying a plurality of procedure codes returned as results based upon the procedure code related information.

2. The charge capture client device of claim 1, wherein:
an E/M code selection display is generated when the E/M code selection graphical interface is selected, the E/M code selection display subsequent in hierarchy to the new bill graphical display, the E/M code selection display including a plurality of selectable Current Procedural Terminology (CPT) codes;
the plurality of procedure codes of the procedure code selection display are CPT or Systematized Nomenclature of Medicine (SNOMED) codes; and
the plurality of diagnosis codes are International Classification of Diseases (ICD) codes.

3. The charge capture client device of claim 1, wherein:
the plurality of template graphical interfaces include a full bill graphical interface for recording the patient identification information, diagnosis code, and E/M code, and a charges template for recording charge information.

4. The charge capture client device of claim 1, further comprising:
a microphone device for capturing the voice utterances, wherein the controller is further configured to initiate the microphone device to capture the voice utterance when the record control graphical interface is selected, and to generate one or more voice files including the voice utterances and temporarily store the one or more voice files in the memory.

5. The charge capture client device of claim 1, wherein:
the open text field for receiving diagnosis related information receives transcribed voice utterance as the diagnosis related information; and
the open text field for receiving procedure code related information receives transcribed voice utterance as the procedure code related information.

* * * * *